(12) United States Patent
Kamon

(10) Patent No.: US 11,416,985 B2
(45) Date of Patent: *Aug. 16, 2022

(54) MEDICAL IMAGE PROCESSING APPARATUS, ENDOSCOPE APPARATUS, DIAGNOSTIC SUPPORT APPARATUS, MEDICAL SERVICE SUPPORT APPARATUS, AND REPORT CREATION SUPPORT APPARATUS

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 16/724,390

(22) Filed: Dec. 23, 2019

(65) Prior Publication Data

US 2020/0143538 A1    May 7, 2020

Related U.S. Application Data

(63) Continuation of application No. PCT/JP2018/020410, filed on May 28, 2018.

(30) Foreign Application Priority Data

Jul. 3, 2017  (JP) .............................. JP2017-130692

(51) Int. Cl.
*G06T 7/00* (2017.01)
*G16H 30/20* (2018.01)
(Continued)

(52) U.S. Cl.
CPC .......... *G06T 7/0012* (2013.01); *A61B 1/0005* (2013.01); *A61B 1/00009* (2013.01);
(Continued)

(58) Field of Classification Search
CPC ......... G06T 7/0012; G06T 2207/10016; G06T 2207/10068; G06T 2207/30096;
(Continued)

(56) References Cited

U.S. PATENT DOCUMENTS 7,965,878 B2    6/2011  Higuchi et al.
8,397,170 B2 *  3/2013  Araoka ................... G16Z 99/00
                                                    715/764
(Continued)

FOREIGN PATENT DOCUMENTS

CN        1725975       1/2006
CN      103079461       5/2013
(Continued)

OTHER PUBLICATIONS

Manfred Jurgen Primus, et al., "Instrument Classification in Laparoscopic Videos." 2015 13th International Workshop on Content-Based Multimedia Indexing, Jun. 10-12, 2015, pp. 1-6.
(Continued)

*Primary Examiner* — Amara Abdi
(74) *Attorney, Agent, or Firm* — JCIPRNET

(57) ABSTRACT

A medical image processing apparatus includes a medical image acquisition unit that acquires the medical image including a subject image, a medical image analysis result acquisition unit that acquires an analysis result obtained by analyzing the medical image, a display unit that displays at least one medical image and at least information on presence or absence of a treatment tool or a type of a treatment tool in the analysis result acquired by the medical image analysis result acquisition unit, and an input receiving unit that receives an input regarding whether or not the information on presence or absence of a treatment tool or a type of a treatment tool included in the analysis result is correct.

22 Claims, 23 Drawing Sheets

(51) Int. Cl.
*G16H 30/40* (2018.01)
*A61B 1/00* (2006.01)

(52) U.S. Cl.
CPC ............. *G16H 30/20* (2018.01); *G16H 30/40* (2018.01); *G06T 2207/10016* (2013.01); *G06T 2207/10068* (2013.01); *G06T 2207/30096* (2013.01)

(58) Field of Classification Search
CPC .......... G06T 7/00; G16H 30/20; G16H 30/40; G16H 10/00; A61B 1/00009; A61B 1/0005; A61B 1/018; A61B 1/00039; A61B 34/20
See application file for complete search history.

(56) References Cited

U.S. PATENT DOCUMENTS

| | | | |
|---|---|---|---|
| 8,423,123 | B2 | 4/2013 | Horn |
| 9,158,382 | B2 | 10/2015 | Asami et al. |
| 9,378,549 | B2 | 6/2016 | Poole et al. |
| 10,231,658 | B2 | 3/2019 | Shiraishi |
| 2006/0274928 | A1* | 12/2006 | Collins ................. G16H 30/40 382/132 |
| 2009/0135249 | A1 | 5/2009 | Hirakawa |
| 2010/0182412 | A1 | 7/2010 | Taniguchi et al. |
| 2014/0184790 | A1* | 7/2014 | Ishihara ................. A61B 1/043 348/135 |
| 2015/0181185 | A1 | 6/2015 | Ikemoto et al. |
| 2016/0259880 | A1* | 9/2016 | Semenyuk ............. G16B 15/00 |
| 2016/0259888 | A1* | 9/2016 | Liu ........................ G16H 30/40 |
| 2016/0331224 | A1* | 11/2016 | Uji ....................... A61B 3/0025 |
| 2019/0328458 | A1* | 10/2019 | Shmayahu ............. A61B 5/742 |

FOREIGN PATENT DOCUMENTS

| | | | |
|---|---|---|---|
| CN | 104027126 | 9/2014 | |
| CN | 104540438 | 4/2015 | |
| EP | 15707777 | 9/2005 | |
| JP | 2007125373 | 5/2007 | |
| JP | 2007195829 | 8/2007 | |
| JP | 2013039230 | 2/2013 | |
| JP | 2013041428 | 2/2013 | |
| JP | 2015085152 | 5/2015 | |
| JP | 2015173737 | 10/2015 | |
| JP | 2016062488 | 4/2016 | |
| JP | 2016158752 | 9/2016 | |
| JP | 2017099509 | 6/2017 | |
| WO | 2009008125 | 1/2009 | |
| WO | 2011152489 | 12/2011 | |
| WO | WO 2011/152489 | * 12/2011 | ........... A61B 1/0005 |
| WO | 2016080121 | 5/2016 | |
| WO | 2016140795 | 9/2016 | |

OTHER PUBLICATIONS

"Search Report of Europe Counterpart Application", dated Jun. 3, 2020, p. 1-p. 7.
Office Action of Japan Counterpart Application, with English translation thereof, dated Jan. 19, 2021, pp. 1-5.
"International Search Report (Form PCT/ISA/210) of PCT/JP2018/020410," dated Aug. 7, 2018, with English translation thereof, pp. 1-5.
"International Preliminary Report on Patentability (Form PCT/IPEA/409) of PCT/JP2018/020410," completed on Oct. 7, 2019, with English translation thereof, pp. 1-17.
Office Action of China Counterpart Application, with English translation thereof, dated Aug. 13, 2021, pp. 1-20.
"Office Action of China Counterpart Application" with English translation thereof, dated Jan. 27, 2022, p. 1-p. 23.

* cited by examiner

MEDICAL IMAGE PROCESSING APPARATUS, ENDOSCOPE APPARATUS, DIAGNOSTIC SUPPORT APPARATUS, MEDICAL SERVICE SUPPORT APPARATUS, AND REPORT CREATION SUPPORT APPARATUS

CROSS-REFERENCE TO RELATED APPLICATIONS

This application is a Continuation of PCT International Application No. PCT/JP2018/020410 filed on May 28, 2018, which claims priority under 35 U.S.C § 119(a) to Japanese Patent Application No. 2017-130692 filed on Jul. 3, 2017. Each of the above application(s) is hereby expressly incorporated by reference, in its entirety, into the present application.

BACKGROUND OF THE INVENTION

1. Field of the Invention

The present invention relates to a medical image processing apparatus, an endoscope apparatus, a diagnostic support apparatus, a medical service support apparatus, and a report creation support apparatus that use an analysis result of a medical image.

2. Description of the Related Art

In the related art, among apparatuses relevant to medical care (hereinafter, referred to as a medical apparatus), an apparatus that acquires an image of a subject (hereinafter, referred to as a medical image) presents the acquired medical image to a doctor. Then, the doctor uses the medical image obtained from the medical apparatus as one of determination materials to perform diagnosis and the like. Needless to say, discrimination of a state of the subject or the like that is performed by using the medical image at the time of diagnosis is based on skill, experience, and the like of the doctor.

In recent years, since image analysis technology has advanced, various types of objective information can be acquired from the medical image by analyzing the medical image. For this reason, the medical apparatus that supports discrimination, diagnosis, and the like by presenting an analysis result of the medical image to a doctor or the like has been on the increase. For example, by analyzing the medical image, it is possible to obtain information on medicine and a treatment tool used in endoscopy (JP2016-062488A). In addition, by analyzing the medical image, it is possible to automatically select a medical image showing a polyp from a series of medical images (JP2007-125373A).

SUMMARY OF THE INVENTION

As described above, the medical apparatus or the like that not only simply obtains the medical image but also supports discrimination, diagnosis, and the like by providing the analysis result of the medical image or a function that uses the analysis result of the medical image has been on the increase. However, the analysis result of the medical images is only one of determination materials for discrimination and diagnosis unless approved by a doctor.

An object of the present invention is to provide a medical image processing apparatus, an endoscope apparatus, a diagnostic support apparatus, a medical service support apparatus, and a report creation support apparatus that can obtain an active and explicit approval to an analysis result of a medical image from a doctor.

A medical image processing apparatus of the present invention comprises a medical image acquisition unit that acquires a medical image including a subject image, a medical image analysis result acquisition unit that acquires an analysis result obtained by analyzing the medical image, a display unit that displays at least one medical image and at least information on presence or absence of a treatment tool or a type of a treatment tool in the analysis result acquired by the medical image analysis result acquisition unit, and an input receiving unit that receives an input of correction information for correcting the information on presence or absence of a treatment tool or a type of a treatment tool included in the analysis result.

It is preferable that the medical image processing apparatus further comprises a selection unit that selects one or more medical images or one or more analysis results relating to the medical images, in which the input receiving unit receives an input of the correction information for the information on presence or absence of a treatment tool or a type of a treatment tool relating to the medical images selected by the selection unit or the information on presence or absence of a treatment tool or a type of a treatment tool relating to the analysis results selected by the selection unit.

It is preferable that the medical image processing apparatus further comprises a storage unit that stores both the analysis result and the correction information in association with the medical image relating to the analysis result and the correction information in a case where the input receiving unit receives an input of the correction information.

It is preferable that the medical image processing apparatus further comprises a storage unit that stores the analysis result, a part or all of which are replaced with contents of the correction information, and the medical image relating to the analysis result, a part or all of which are replaced with contents of the correction information, in association with each other, in a case where the input receiving unit receives an input of the correction information.

It is preferable that the display unit sequentially displays one or more medical images, or displays a plurality of the medical images collectively, and a reception of an input by the input receiving unit is validated after the display unit displays all of the medical images to be displayed at least once.

It is preferable that the medical image processing apparatus further comprises a medical image analysis processing unit that detects a region of interest, which is a region to be observed, based on a feature amount of pixels of the medical image and obtains at least the information on presence or absence of a treatment tool or a type of a treatment tool for the region of interest, in which the medical image analysis result acquisition unit acquires the analysis result from the medical image analysis processing unit.

It is preferable that the medical image analysis result acquisition unit acquires the analysis result from a recording apparatus that records the analysis result relating to the medical image.

It is preferable that the medical image is a normal light image obtained by emitting light in a white band or light in a plurality of wavelength bands as the light in the white band.

It is preferable that the medical image is an image obtained by emitting light in a specific wavelength band, and the specific wavelength band is a band narrower than a white wavelength band.

It is preferable that the specific wavelength band is a blue band or a green band of a visible range.

It is preferable that the specific wavelength band includes a wavelength band of 390 nm to 450 nm or a wavelength band of 530 nm to 550 nm, and the light in the specific wavelength band has a peak wavelength in the wavelength band of 390 nm to 450 nm or the wavelength band of 530 nm to 550 nm.

It is preferable that the specific wavelength band is a red band of a visible range.

It is preferable that the specific wavelength band includes a wavelength band of 585 nm to 615 nm or a wavelength band of 610 nm to 730 nm, and the light in the specific wavelength band has a peak wavelength in the wavelength band of 585 nm to 615 nm or the wavelength band of 610 nm to 730 nm.

It is preferable that the specific wavelength band includes a wavelength band in which light absorption coefficients of oxygenated hemoglobin and reduced hemoglobin are different, and the light in the specific wavelength band has a peak wavelength in the wavelength band in which the light absorption coefficients of oxygenated hemoglobin and reduced hemoglobin are different.

It is preferable that the specific wavelength band includes a wavelength band of 400±10 nm, 440±10 nm, 470±10 nm, or 600 nm to 750 nm, and the light in the specific wavelength band has a peak wavelength in the wavelength band of 400±10 nm, 440±10 nm, 470±10 nm, or 600 nm to 750 nm.

It is preferable that the medical image is an in-vivo image obtained by imaging an inside of a living body, and the in-vivo image has information on fluorescence emitted from a fluorescent material in the living body.

It is preferable that the fluorescence is fluorescence obtained by emitting excitation light having a peak wavelength of 390 nm to 470 nm to an inside of the living body.

It is preferable that the medical image is an in-vivo image obtained by imaging an inside of a living body, and the specific wavelength band is a wavelength band of infrared light.

It is preferable that the specific wavelength band includes a wavelength band of 790 nm to 820 nm or a wavelength band of 905 nm to 970 nm, and the light in the specific wavelength band has a peak wavelength in the wavelength band of 790 nm to 820 nm or the wavelength band of 905 nm to 970 nm.

It is preferable that the medical image acquisition unit has a special light image acquisition section that acquires a special light image having a signal in a specific wavelength band based on a normal light image obtained by emitting light in a white band or light in a plurality of wavelength bands as the light in the white band, and the medical image is the special light image.

It is preferable that the signal in the specific wavelength band is obtained by calculation based on color information of RGB or CMY included in the normal light image.

It is preferable that the medical image processing apparatus further comprises a feature amount image generation unit that generates a feature amount image by calculation based on at least one of a normal light image obtained by emitting light in a white band or light in a plurality of wavelength bands as the light in the white band or a special light image obtained by emitting light in a specific wavelength band, the medical image is the feature amount image.

An endoscope apparatus of the present invention comprises the medical image processing apparatus, and an endoscope that acquires an image by emitting at least one of light in a white wavelength band or light in a specific wavelength band.

A diagnostic support apparatus of the present invention comprises the medical image processing apparatus A medical service support apparatus of the present invention comprises the medical image processing apparatus A report creation support apparatus of the present invention comprises the medical image processing apparatus, and a report creating unit that creates a report using the analysis result.

The medical image processing apparatus, the endoscope apparatus, the diagnostic support apparatus, the medical service support apparatus, and the report creation support apparatus of the present invention can obtain an active and explicit approval to the analysis result of the medical image from a doctor.

DESCRIPTION OF THE PREFERRED EMBODIMENTS

First Embodiment

Figure 1:
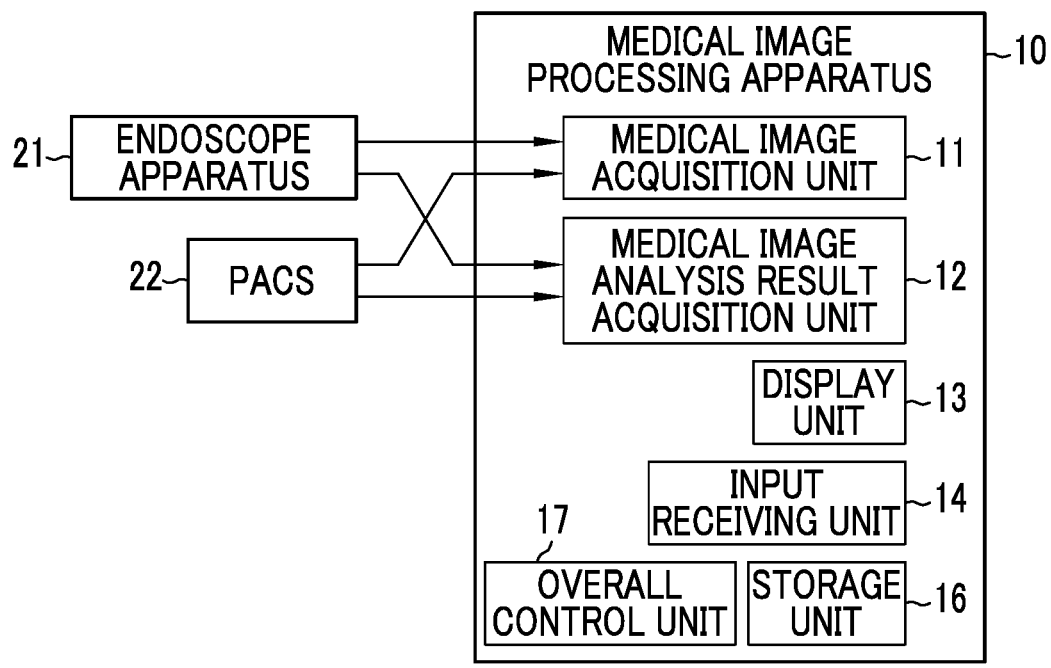
FIG. 1 is a block diagram of a medical image processing apparatus.

As shown in FIG. 1, a medical image processing apparatus 10 comprises a medical image acquisition unit 11, a medical image analysis result acquisition unit 12, a display unit 13, an input receiving unit 14, a storage unit 16, and an overall control unit 17.

The medical image acquisition unit 11 acquires a medical image 50 including a subject image, for example, directly from a modality, such as an endoscope apparatus 21 that is a medical apparatus, or through a management system, such as a picture archiving and communication system (PACS) 22 in which the medical images 50 (refer to FIG. 5 or the like) acquired by various modalities are stored, or other information systems. The medical image 50 acquired by the medical image acquisition unit 11 depends on a modality that obtains the medical image 50. That is, the medical image 50 acquired from the endoscope apparatus 21 is a so-called endoscopic image. The medical image 50 acquired from an ultrasound examination apparatus (not shown) is a so-called ultrasound image. In a case of acquiring a medical image from an X-ray imaging apparatus (not shown), the acquired medical image 50 is a so-called X-ray image. In a case of acquiring the medical image 50 from a computed tomography (CT) scanner or a magnetic resonance imaging (MM) examination apparatus (neither are shown), a reconstructed image is the medical image 50. The same applies to a case of acquiring the medical image 50 from other modalities. In addition, the same applies to a case of acquiring the medical image 50 through a management system such as the PACS 22, or other information systems. Further, the medical image 50 is a still image or a motion picture. In a case where the medical image 50 is a motion picture, display of the medical image 50 includes not only displaying a still image of one representative frame forming the motion picture but also reproducing the motion picture once or multiple times.

In a case where there are a plurality of the medical images 50 in the endoscope apparatus 21, the PACS 22, or the like, the medical image acquisition unit 11 can select and acquire all or a part of a plurality of the medical images 50. In a case of selecting and acquiring a part of medical images 50 from a plurality of the medical images 50 in the endoscope apparatus 21, the PACS 22, or the like, it is possible to manually select the medical images 50 in accordance with a user operation of a doctor or the like. In addition, the medical image acquisition unit 11 can automatically select the medical images 50 to be acquired according to the imaging date and time, an imaging part, or other conditions set in advance.

The medical image analysis result acquisition unit 12 acquires a result of analysis (hereinafter, referred to as an analysis result) of the medical image 50 including a subject image, for example, directly from a modality, such as the endoscope apparatus 21 that is a medical apparatus, or through a management system, such as the PACS 22 in which the medical images 50 acquired by various modalities are stored, or other information systems. The medical image analysis result acquisition unit 12 can acquire any analysis result of the medical image 50 from the endoscope apparatus 21, the PACS 22, or the like. However, in a case where there is an analysis result of the medical image 50 acquired by the medical image acquisition unit 11, the medical image analysis result acquisition unit 12 acquires the analysis result of at least the medical image 50 acquired by the medical image acquisition unit 11.

The analysis result of the medical image is a result obtained by image analysis of the medical image 50. More specifically, the medical image analysis result includes, for example, one or a plurality of pieces of information on presence or absence of a lesion (including presence or absence of a portion that may be a lesion and a case of information on a position, a size, a range, or the like of a lesion or a portion that may be a lesion), a type of a lesion (including the properties of a subject in a case where there is no lesion; for example, neoplasm, non-neoplasm, normal, unknown, and the like), presence or absence of a treatment mark (for example, a trace of surgical treatment or a trace of treatment using a drug, radiation, or the like), a type of treatment mark, drug (for example, fluorescent drug) administered (including administration by spraying, injection, application, and the like) to the subject, presence or absence of reflection of an instrument such as a treatment tool, and a type of an instrument such as a reflected treatment tool.

Figure 2:
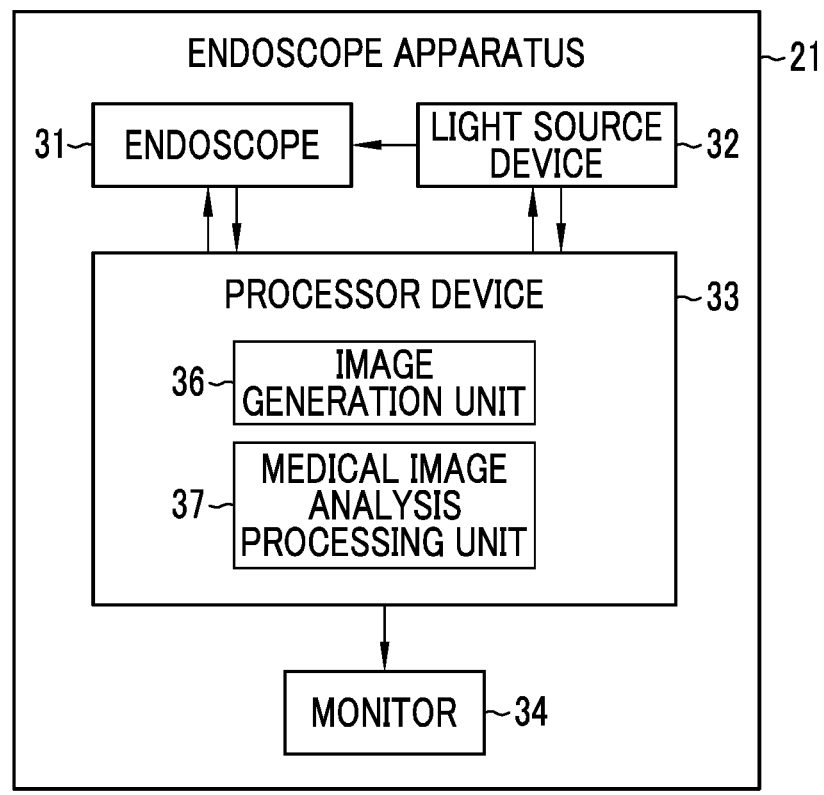
FIG. 2 is a block diagram of an endoscope apparatus.

In the present embodiment, as shown in FIG. 2, the endoscope apparatus 21 has an endoscope 31 that emits at least one of light in a white wavelength band or light in a specific wavelength band to acquire an image, a light source device 32 that emits illumination light to the inside of the subject through the endoscope 31, a processor device 33, and a monitor 34 for displaying the medical image 50 (endoscopic image) or the like captured by using the endoscope 31. Then, the processor device 33 comprises an image generation unit 36 that generates the medical image 50 (endoscopic image) and a medical image analysis processing unit 37 that analyzes the medical image 50 (endoscopic image) and obtains the analysis result.

In the present embodiment, the medical image processing apparatus 10 is connected to the endoscope apparatus 21 to acquire the medical image 50 (endoscopic image), and an analysis result of the medical image 50 (endoscopic image) from the endoscope apparatus 21. Specifically, the medical image processing apparatus 10 is connected to the processor device 33. Then, the medical image acquisition unit 11 acquires the medical image 50 (endoscopic image) from the image generation unit 36, and the medical image analysis result acquisition unit 12 receives the analysis result of the medical image 50 (endoscopic image) from the medical image analysis processing unit 37. As described above, the medical image acquired by the medical image acquisition unit 11 is specifically an endoscopic image. However, unless otherwise required to distinguish therebetween particularly, for the sake of simplicity, in the following, all of the medical images 50 acquired by the medical image acquisition unit 11 are referred to as the medical image 50. In addition, in the present embodiment, the medical image analysis processing unit 37 obtains at least information on presence or absence of a treatment tool or a type of a treatment tool, as the analysis result of the medical image 50. For this reason, the medical image analysis result acquisition unit 12 can acquire, from the medical image analysis processing unit 37, at least information on presence or absence of a treatment tool or a type of a treatment tool as the analysis result of the medical image 50 acquired by the medical image acquisition unit 11.

Figure 3:
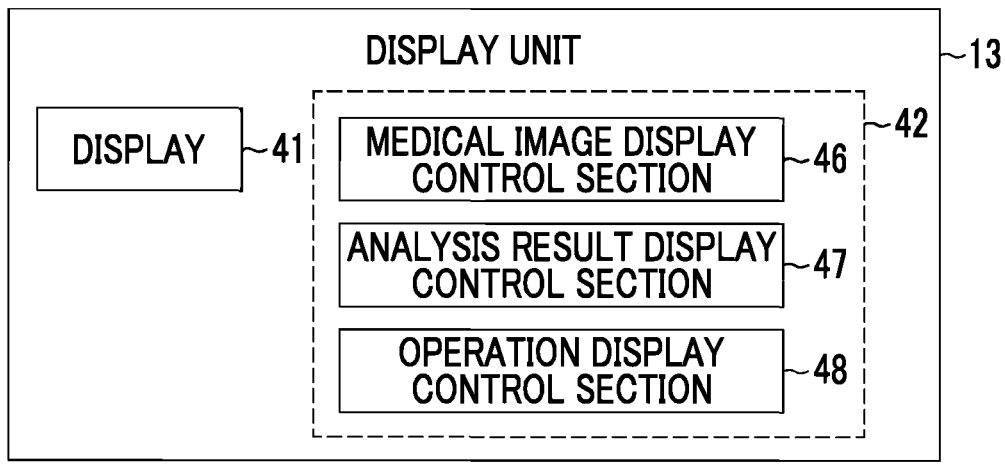
FIG. 3 is a block diagram of a display unit.

The display unit 13 displays at least one medical image 50 and at least information on presence or absence of a treatment tool or a type of a treatment tool among the analysis results acquired by the medical image analysis result acquisition unit 12. As shown in FIG. 3, the display unit 13 comprises a display 41 and a display control section 42 that controls a display aspect on the display screen 51 of the display 41. Then, the display control section 42 comprises a medical image display control section 46, an analysis result display control section 47, and an operation display control section 48.

Figure 5:
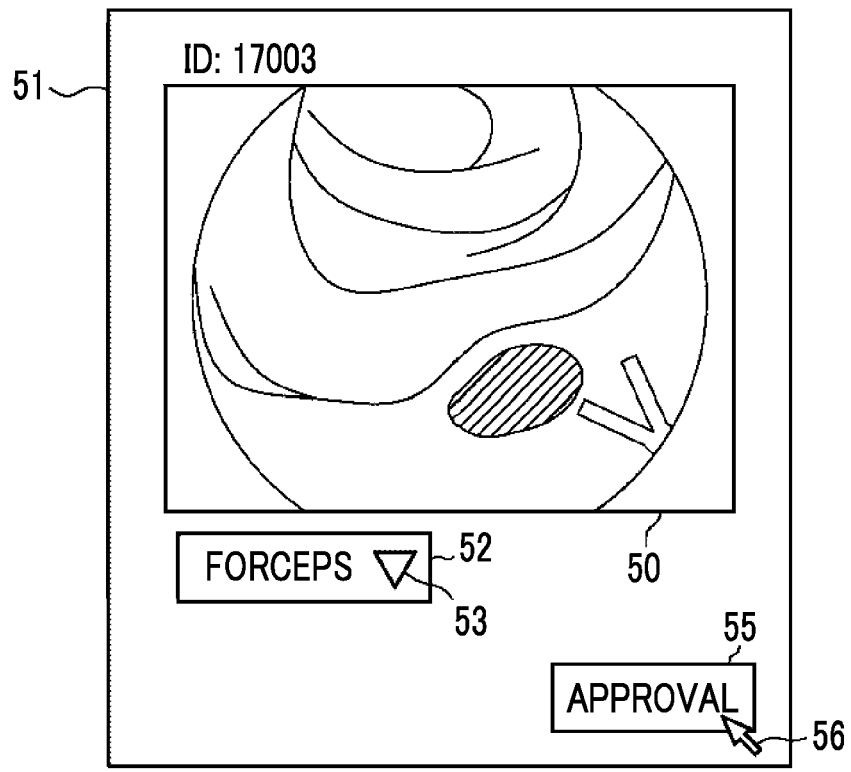
FIG. 5 is a display screen.

The display 41 includes a display screen 51 (refer to FIG. 5 or the like) on which the medical image 50 acquired by the medical image acquisition unit 11 and the analysis result of the medical image 50 acquired by the medical image analysis result acquisition unit 12 are displayed. As shown in FIG. 5 or the like, by displaying the medical image 50 and the analysis result of the medical image 50 collectively, a user can check the medical image 50 and approve and correct the analysis result of the medical image 50. In the present embodiment, the display 41 is provided in the medical image processing apparatus 10 and is different from the monitor 34 of the endoscope apparatus 21 to which the medical image processing apparatus 10 is connected. Here, the display 41 can be commonly used as a monitor or display of a device or a system such as the endoscope apparatus 21 to which the medical image processing apparatus 10 is connected.

The medical image display control section 46 controls a position, a size, and the like for displaying the medical image 50 acquired by the medical image acquisition unit 11. In addition, in a case where the medical image acquisition unit 11 acquires a plurality of medical images 50, the medical image display control section 46 can display one or a plurality of medical images 50 among a plurality of the medical images 50 on the display screen 51. In a case where a plurality of medical images are displayed on the display screen 51, the medical image display control section 46 also controls the display order (array) of a plurality of the medical images 50. In addition, in a case where the medical image 50 displayed on the display screen 51 is subjected to a click operation or the like, the medical image display control section 46 may enlarge the medical image 50 to be displayed, for example. In this case, the medical image display control section 46 controls generation of a window (display region) for displaying the medical image 50 to be enlarged and control of an enlargement ratio.

In a case where there is an analysis result acquired by the medical image analysis result acquisition unit 12 for the medical image 50 to be displayed on the display screen 51, the analysis result display control section 47 controls a display position or the like of the analysis result relating to the medical image 50 to be displayed on the display screen 51 in accordance with a display position of the medical image 50. In addition, in a case where there are a plurality of analysis results relating to one medical image 50 displayed on the display screen 51, the analysis result display control section 47 can select one or a plurality of analysis results for one medical image 50, or display all of the analysis results on the display screen 51. In a case where a part of a plurality of the analysis results is displayed on the display screen 51, the analysis result display control section 47 selects one or a plurality of analysis results to be displayed on the display screen 51 in accordance with display setting of the analysis results. In the present embodiment, information on presence or absence of a treatment tool or a type of a treatment tool among the analysis results acquired by the medical image analysis result acquisition unit 12 is displayed. In the present embodiment, the "information on presence or absence of a treatment tool or a type of a treatment tool" to be displayed refers to, for example, "forceps", "snare", "knife" (high-frequency knife, or the like), "brush" (for cytology, or the like), "hood", or "none" (meaning that a treatment tool is not reflected).

The operation display control section 48 provides an operation display such as a button, a switch, a check box, or a scroll bar on the display screen 51. In addition, the operation display control section 48 controls a pointer, a cursor, or the like relating to an operation of a pointing device such as a mouse.

In the present embodiment, the operation display control section 48 provides a pull-down menu display button 53 in the analysis result display field 52 for displaying the analysis result. The pull-down menu display button 53 is operated in a case where it cannot be said that "information on presence or absence of a treatment tool or a type of a treatment tool", which is the analysis result displayed in the analysis result display field 52, is correct (it cannot be approved as at least correct information). Accordingly, it is possible to correct the analysis result displayed in the analysis result display field 52 to the information that is correct (at least not erroneous) using a pull-down menu 54 (refer to see FIG. 6) optionally. The correction operation using the pull-down menu 54 is an input of correction information for correcting information on presence or absence of a treatment tool or a type of a lesion included in the analysis result.

In addition, in the present embodiment, the operation display control section 48 provides an approval button 55 (refer to FIG. 5 and the like) on the display screen 51. The approval button 55 actively and explicitly gives an approval to the analysis result displayed in the analysis result display field 52. Therefore, the approval button 55 is operated in a case where the analysis result displayed in the analysis result display field 52 (or contents input using the pull-down menu 54) is actively and explicitly approved as being correct. In addition to this, in the present embodiment, the operation display control section 48 displays a pointer 56 relating to an operation of a pointing device (not shown) on the display screen 51.

As described above, the medical image 50 and the analysis result of the medical image 50 are displayed on the display screen 51, and in addition to this, the display control section 42 can display information on a patient such as a name and other information on the medical image 50 such as an identification (ID) number for identifying the medical image 50, a name of an observation site, or imaging date and time on the display screen 51 appropriately according to display setting.

The input receiving unit 14 receives an input from a mouse, a keyboard, and other operation devices for performing operation input using various displays for an operation to be displayed on the display screen 51 by the operation display control section 48. The operation for receiving an input by the input receiving unit 14 includes operations of the pull-down menu display button 53, the pull-down menu 54, and the approval button 55 in the analysis result display field 52. The operations of the pull-down menu display button 53, the pull-down menu 54, and the approval button 55 are operations to perform an input regarding whether or not "information on presence or absence of a treatment tool or a type of a treatment tool" displayed in the analysis result display field 52 among information pieces included in the analysis result is correct. Therefore, in the present embodiment, the input receiving unit 14 receives an input regarding whether or not at least information on presence or absence of a treatment tool or a type of a treatment tool included in the analysis result is correct. In addition, a reception of the correction operation using the pull-down menu 54 is a reception of an input of correction information for correcting information on presence or absence of a treatment tool or a type of a treatment tool included in the analysis result. That is, in the present embodiment, the input receiving unit 14 receives an input of correction information for correcting at least information on presence or absence of a treatment tool or a type of a treatment tool included in the analysis result.

In a case where the approval button 55 is operated, the storage unit 16 stores the medical image 50 displayed on the display screen 51 and the analysis result displayed in the analysis result display field 52 (including a case where the contents are corrected using the pull-down menu 54) in association with each other. In the present embodiment, the storage unit 16 stores the information on presence or absence of a treatment tool or a type of a treatment tool, for which the input regarding whether or not the information is correct is received by the input receiving unit 14, and the medical image 50 relating to "the information on presence or absence of a treatment tool or a type of a treatment tool", for which the input regarding whether or not the information is correct is received by the input receiving unit, in association with each other. In addition, in the present embodiment, the storage unit 16 includes a memory, a hard disk, and other storages, for example. For this reason, the storage unit 16 stores an approved combination of the medical image 50 and the analysis result in the storage unit 16 itself in association with each other. Here, the storage unit 16 can store the approved combination of the medical image 50 and the analysis result in a storage (not shown) provided in a management system such as the PACS 22, other information systems, the endoscope apparatus 21 or the like, or other external storages such as a network attached storage (NAS) in association with each other.

The overall control unit 17 controls an overall operation of each unit of the medical image processing apparatus 10. For example, the overall control unit 17 realizes the operation of the medical image processing apparatus 10 corresponding to various operations of the pull-down menu display button 53, the pull-down menu 54, the approval button 55, or the like displayed on the display screen 51.

Figure 4:
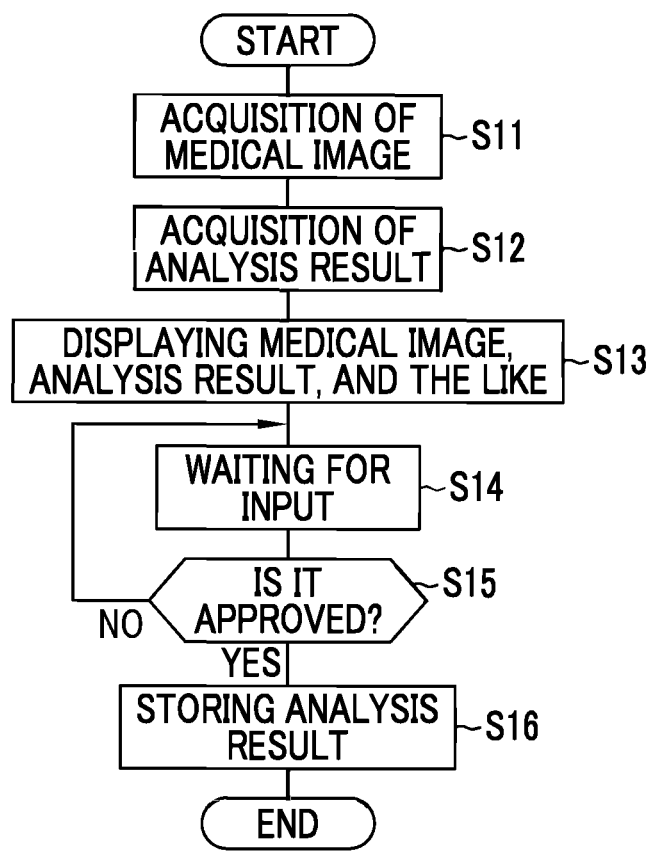
FIG. 4 is a flowchart showing an operation of the medical image processing apparatus.

Hereinafter, an operation flow of the medical image processing apparatus 10 configured as the above will be described. As shown in FIG. 4, the medical image acquisition unit 11 acquires one or a plurality of medical images 50 from the endoscope apparatus 21 or the like automatically or by manual selection (step S11). In addition, the medical image analysis result acquisition unit 12 acquires analysis results relating to one or a plurality of medical images 50 from the endoscope apparatus 21 or the like automatically or by manual selection (step S12).

In a case where the medical image 50 and the analysis result are acquired, as shown in FIG. 5, the display unit 13 displays the medical image 50 on the display screen 51 and displays an analysis result relating to the medical images 50 ("forceps" in FIG. 5) displayed on the display screen 51 in the analysis result display field 52 (step S13). At this time, the operation display control section 48 displays the pull-down menu display button 53 in the analysis result display field 52 and allows the analysis result displayed in the analysis result display field 52 to be corrected. In addition, the operation display control section 48 displays an approval button 55 on the display screen 51, and allows the analysis result displayed in the analysis result display field 52 or the analysis result corrected using the pull-down menu 54 to be approved. These operations of the approval button 55 and the like can be performed using a pointer 56, for example.

In a case where the medical image 50 and the analysis result are displayed on the display screen 51, the input receiving unit 14 waits for a reception of an input (step S14). At this time, the doctor refers to the medical image 50 displayed on the display screen 51, the analysis result ("forceps") displayed in the analysis result display field 52, and the like to discriminate or diagnose the subject.

In a case where the analysis result displayed in the analysis result display field 52 is correct and can be approved as it is, the doctor operates a pointing device, for example, and as a result, clicks the approval button 55 with the pointer 56. In a case where the approval button 55 is clicked, the input receiving unit 14 receives a click on the approval button 55. Accordingly, the doctor actively and explicitly gives an approval to the analysis result displayed in the analysis result display field 52 (step S15: YES).

Then, in a case where the input receiving unit 14 receives a click on the approval button 55, the storage unit 16 stores the medical image 50 displayed on the display screen 51 and the analysis result displayed in the analysis result display field 52 in association with each other (step S16). In a case where the storage unit 16 stores the medical image 50 and the analysis result in association with each other, the display unit 13 displays the medical image 50 to be displayed next, the analysis result, and the like on the display screen 51. Accordingly, the medical image processing apparatus 10 sequentially displays one or more medical images 50 and the like on the display screen 51.

Figure 6:
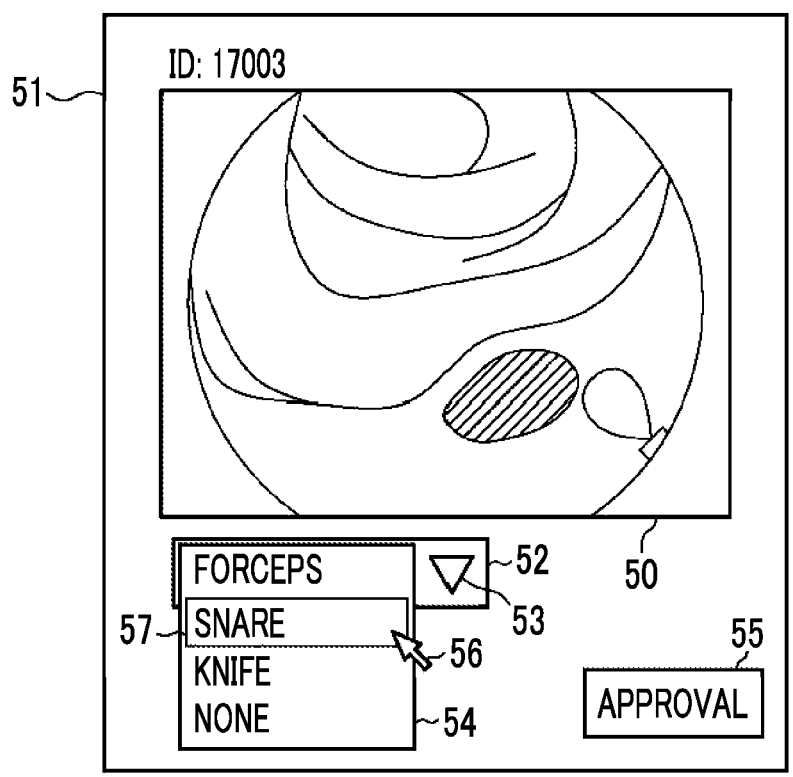
FIG. 6 is a display screen in a case of correcting an analysis result.

On the other hand, in a case where the analysis result displayed in the analysis result display field 52 is not correct and the analysis result displayed in the analysis result display field 52 is not approved (step S15: NO), as shown in FIG. 6, the doctor clicks the pull-down menu display button 53 with the pointer 56. Then, the operation display control section 48 displays the pull-down menu 54 in the analysis result display field 52. In the present embodiment, the analysis result to be displayed in the analysis result display field 52 is "the information on presence or absence of a treatment tool or a type of a treatment tool", specifically "forceps", "snare", "knife", or "none". For this reason, the operation display control section 48 displays a list of items of "forceps", "snare", "knife", or "none" in the pull-down menu 54. In addition, the operation display control section 48 attaches a selection mark 57 to an item (item "snare" in FIG. 6) on which the pointer 56 is superimposed.

In a case where the input receiving unit 14 receives a click on an item in the pull-down menu 54, the analysis result display control section 47 corrects the item to be displayed in the analysis result display field 52 to the item selected by clicking in the pull-down menu 54. Thereafter, the approval button 55 is clicked, and as a result, an approval is actively and explicitly given to the corrected analysis result (step S15: YES). In a case where the corrected analysis result is approved in this way, the storage unit 16 stores the medical image 50 displayed on the display screen 51 and the analysis result displayed in the analysis result display field 52 in association with each other (step S16).

As described above, the medical image processing apparatus 10 can obtain an active and explicit approval to the analysis result of the medical image 50 from the doctor. In particular, in the present embodiment, an active and explicit approval can be obtained for at least information on presence or absence of a treatment tool or a type of a treatment tool among the analysis results relating to the medical image 50.

In addition, in a case where the doctor does not approve the analysis result as it is in a case where the analysis result of the medical image 50 is not correct, or the like, the medical image processing apparatus 10 gives an opportunity to input the correction information for correcting the analysis result of the medical image 50, as an aspect of an approval operation. For this reason, the doctor does not have to necessarily receive the analysis result of the medical image 50, and can correct the analysis result optionally and easily (including leaving one to be corrected as a log) according to his/her own determination.

Figure 7:
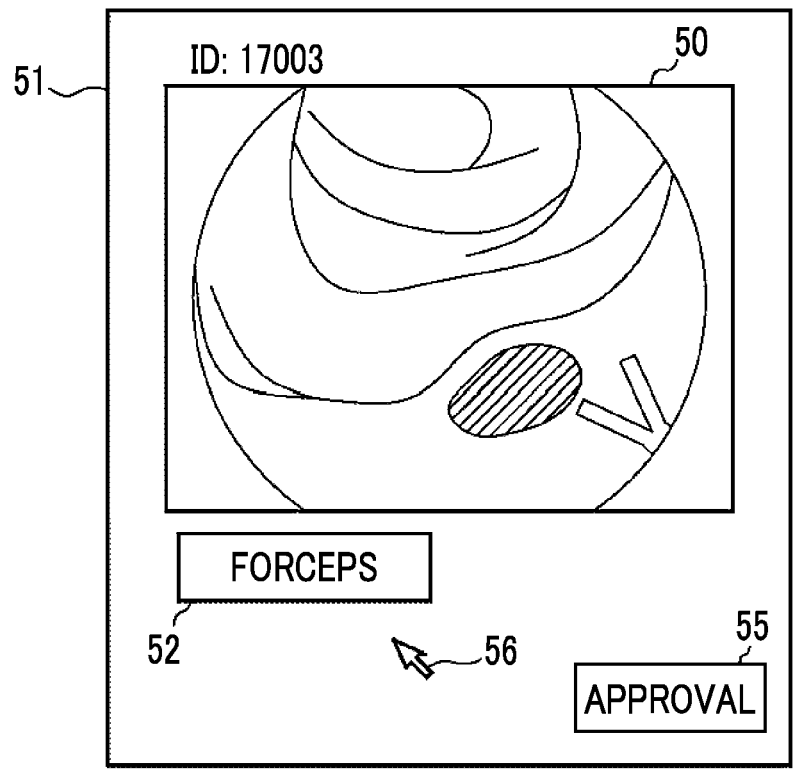
FIG. 7 is a display screen in which an analysis result display field is used as a correction item display button.
Figure 8:
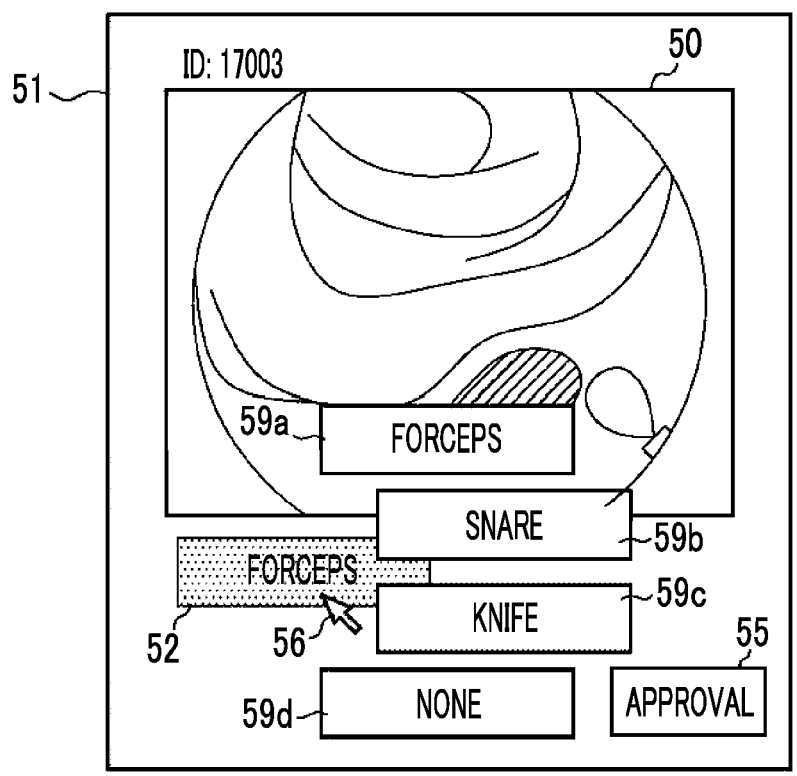
FIG. 8 is a display screen in which an analysis result display field is used as a correction item display button.

Further, in the first embodiment, the pull-down menu display button 53 is displayed in the analysis result display field 52, and the correction information for the analysis result is input using the pull-down menu display button 53 and the pull-down menu 54. However, it is possible to receive an input of the correction information in other forms. For example, as shown in FIG. 7, the analysis result display field 52 itself is used as a correction item display button for displaying items (correction items) representing the correction information. That is, the analysis result display field 52 is used as the correction item display button. Then, as shown in FIG. 8, in a case where the analysis result display field 52 is clicked with the pointer 56, for example, around the analysis result display field 52, correction items 59a to 59d of "forceps", "snare", "knife", or "none" are displayed, and one of these is selected by clicking with the pointer 56 or the like. Accordingly, it is possible to input the correction item of the analysis result. In addition this, for example, in a case where the analysis result display field 52 is set as a region in which an input can be performed, it is possible to input the correction information with any word using a character input device such as a keyboard instead of selecting a correction item. In the following, the same applies to a case where correction information is input using the pull-down menu display button 53 and the pull-down menu 54.

In the first embodiment, the approval button 55 is displayed on the display screen 51. However, instead of the operation of the approval button 55, it may be possible to perform the approval operation by a gesture input for performing an input using a movement trajectory of the pointer 56. In addition, it may be possible to perform the approval operation using not only the pointing device but also other devices (such as a physical button or a switch provided in the medical image processing apparatus 10).

Second Embodiment

In the first embodiment, as an example, one medical image 50 is displayed on the display screen 51. However, it is possible to display a plurality of the medical images 50 collectively on the display screen 51. In the second embodiment, an example in which a plurality of the medical images 50 are displayed on the display screen 51 is described, but a configuration of the medical image processing apparatus 10 is the same as that of the first embodiment.

Figure 9:
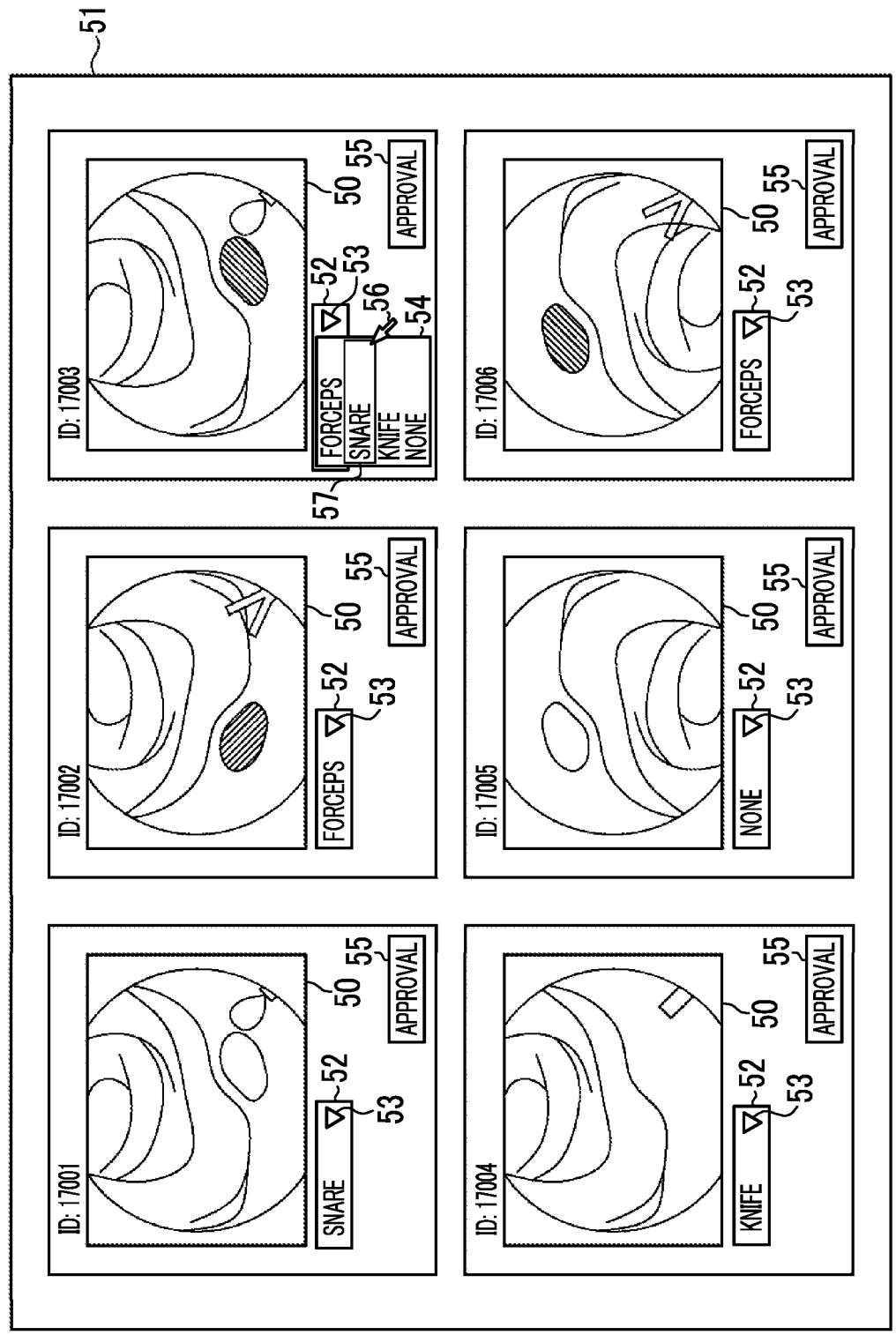
FIG. 9 is a display screen on which a plurality of medical images are displayed.

As shown in FIG. 9, in a case where a plurality of the medical images 50 are displayed on the display screen 51, the approval button 55 can be provided for each medical image 50, for example. In addition, since the analysis result is different for each medical image 50, the analysis result display field 52 and the pull-down menu display button 53 are provided for each medical image 50 to display the analysis result. In this case, it is possible to obtain an active and explicit approval to the analysis result for each medical image 50.

Figure 10:
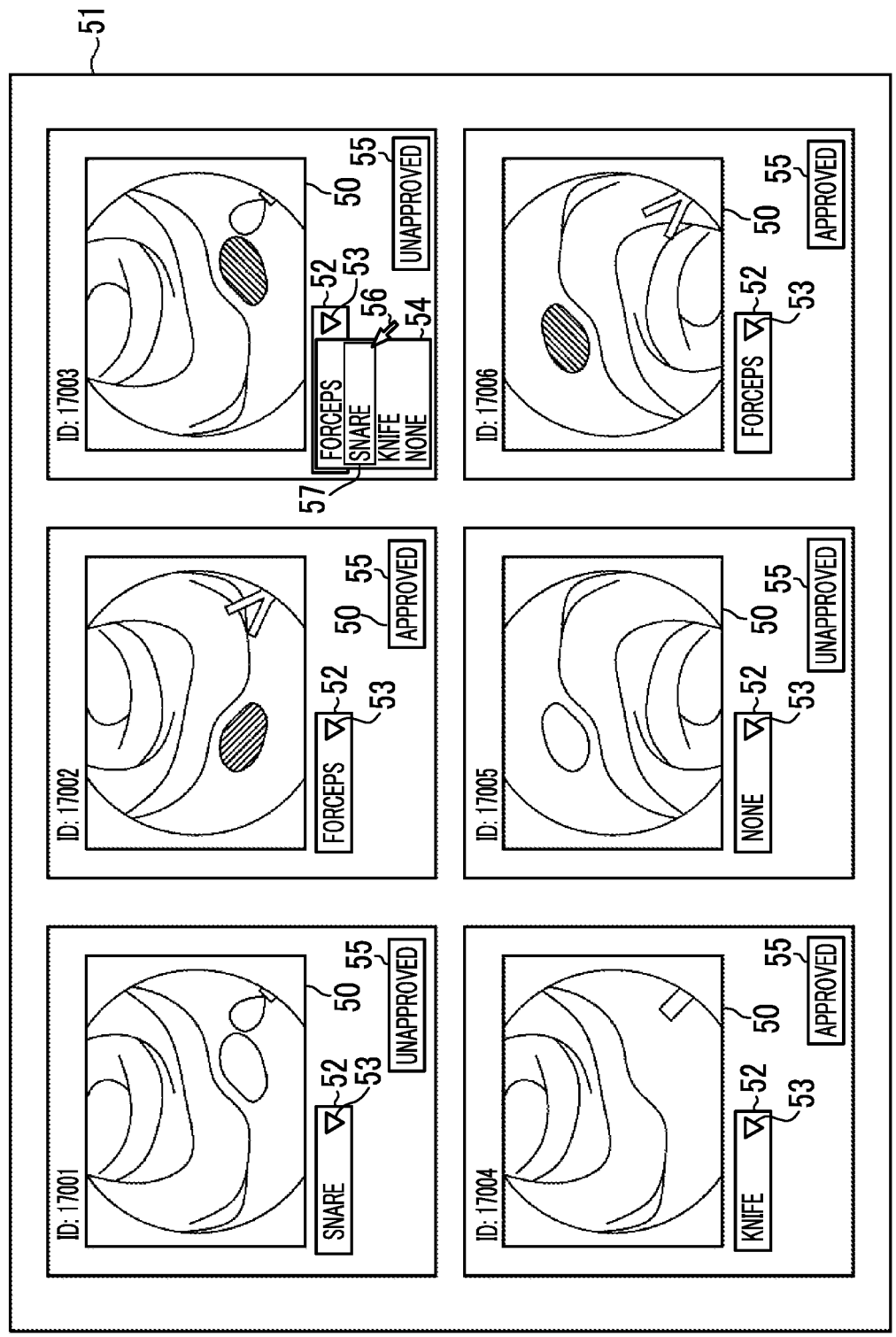
FIG. 10 is a display screen on which a plurality of medical images are displayed.

As shown in FIG. 10, in a case where a plurality of the medical images 50 are displayed on the display screen 51 and the approval button 55 is provided for each medical image 50 respectively, it is preferable that each approval button 55 shows whether or not the approval operation has been performed. In FIG. 10, "unapproved" is displayed in the approval button 55 for the medical image 50 for which the approval operation has not been completed, and "approved" is displayed in the approval button 55 for the medical image 50 for which the approval operation has been completed. In this way, even in a case where a plurality of the medical images 50 and approval buttons 55 are displayed on the display screen 51, it is clear whether the approval operation has been completed for each medical image 50, and the approval operation is not forgotten.

Figure 11:
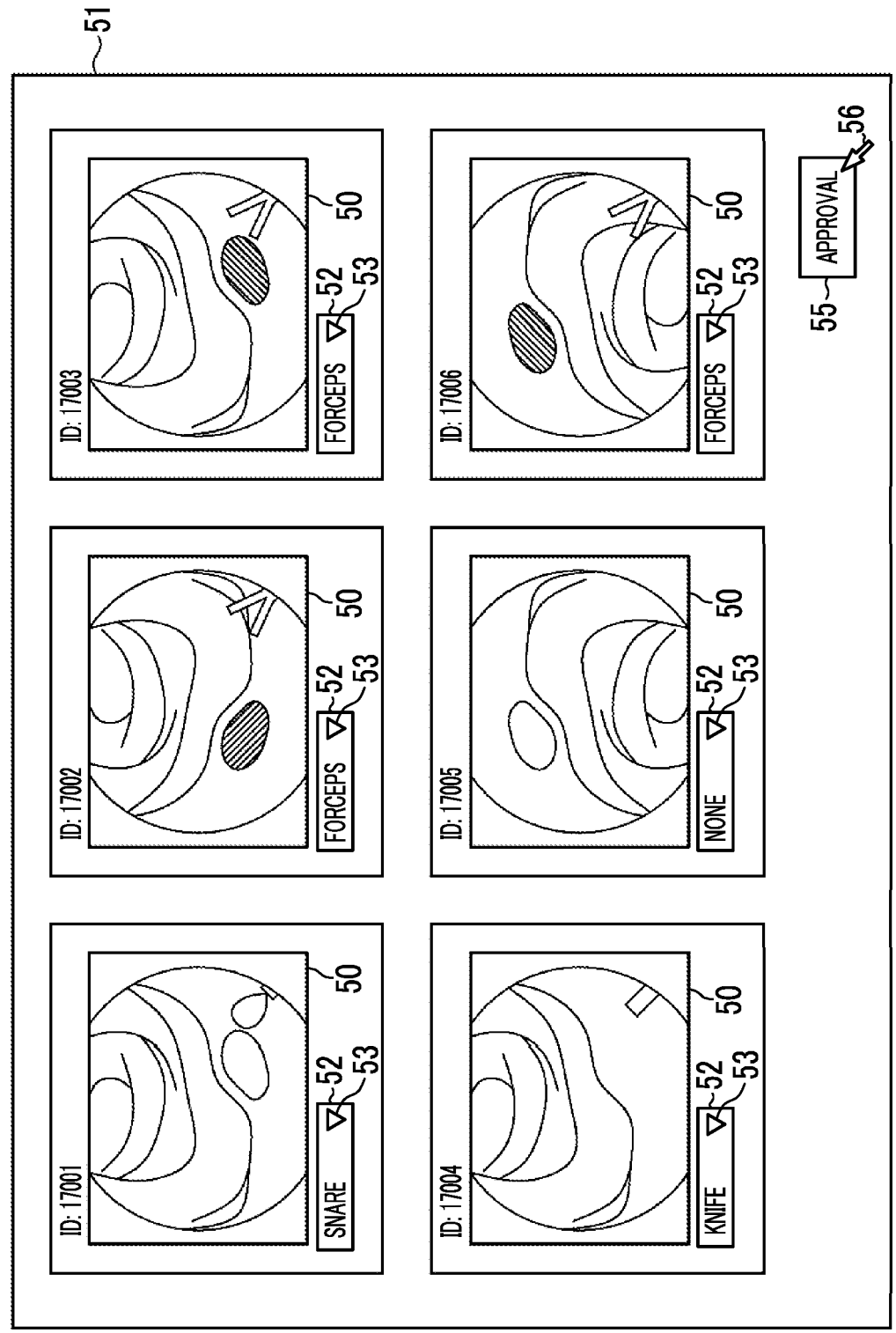
FIG. 11 is a display screen on which a plurality of medical images are displayed.

In FIGS. 9 and 10, the approval button 55 is displayed for each medical image 50 respectively, but instead of displaying the approval button 55 for each medical image 50 respectively, as shown in FIG. 11, it is possible to display a representative approval button 55 for giving an approval to a combination of all of the medical images 50 and the analysis results simultaneously. In this case, it is not necessary to perform an approval operation for each of a plurality of the medical images 50 and the analysis results respectively, and thus, the approval operation can be performed more easily.

Figure 12:
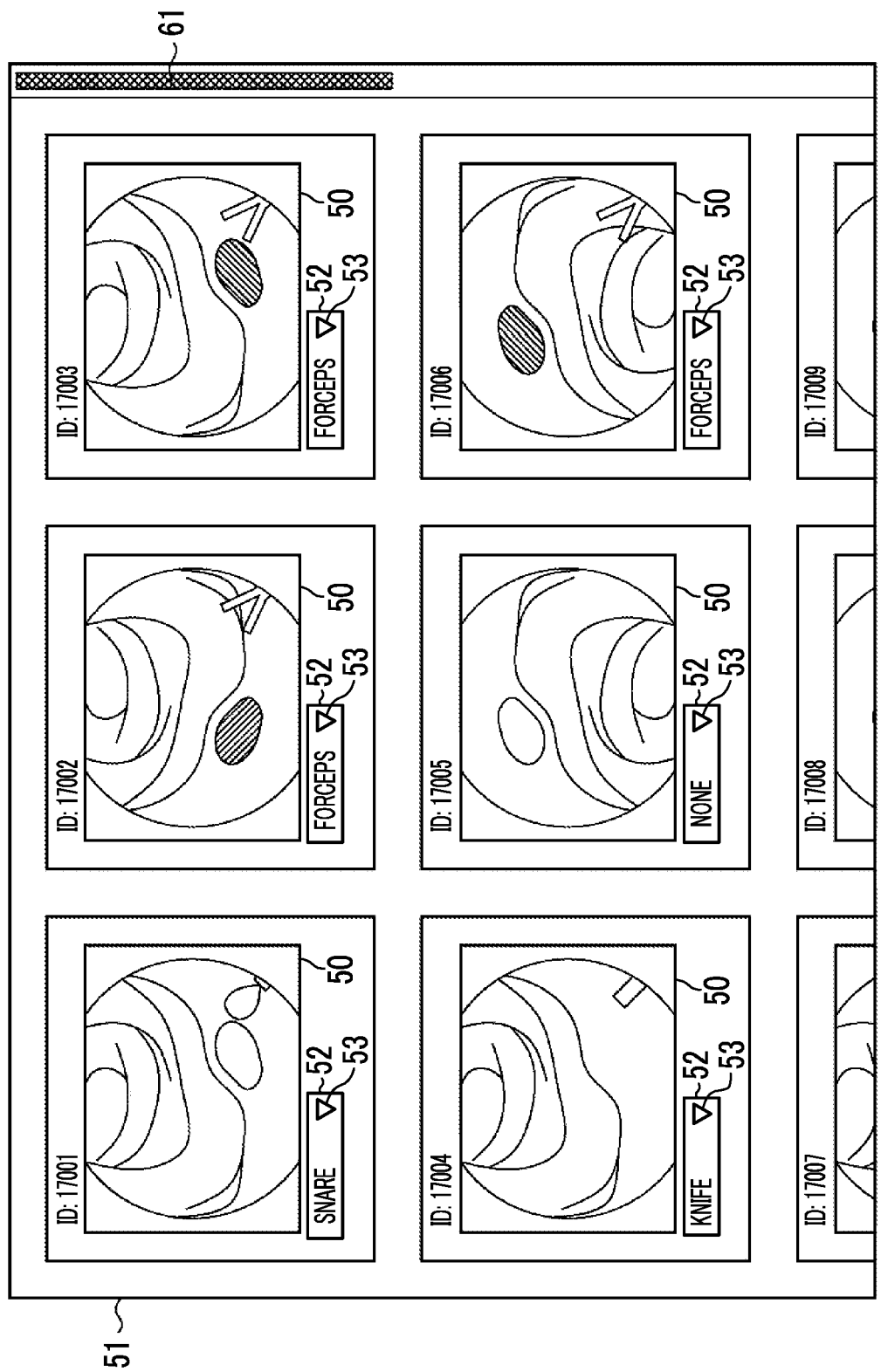
FIG. 12 is a display screen on which a plurality of medical images are displayed.
Figure 13:
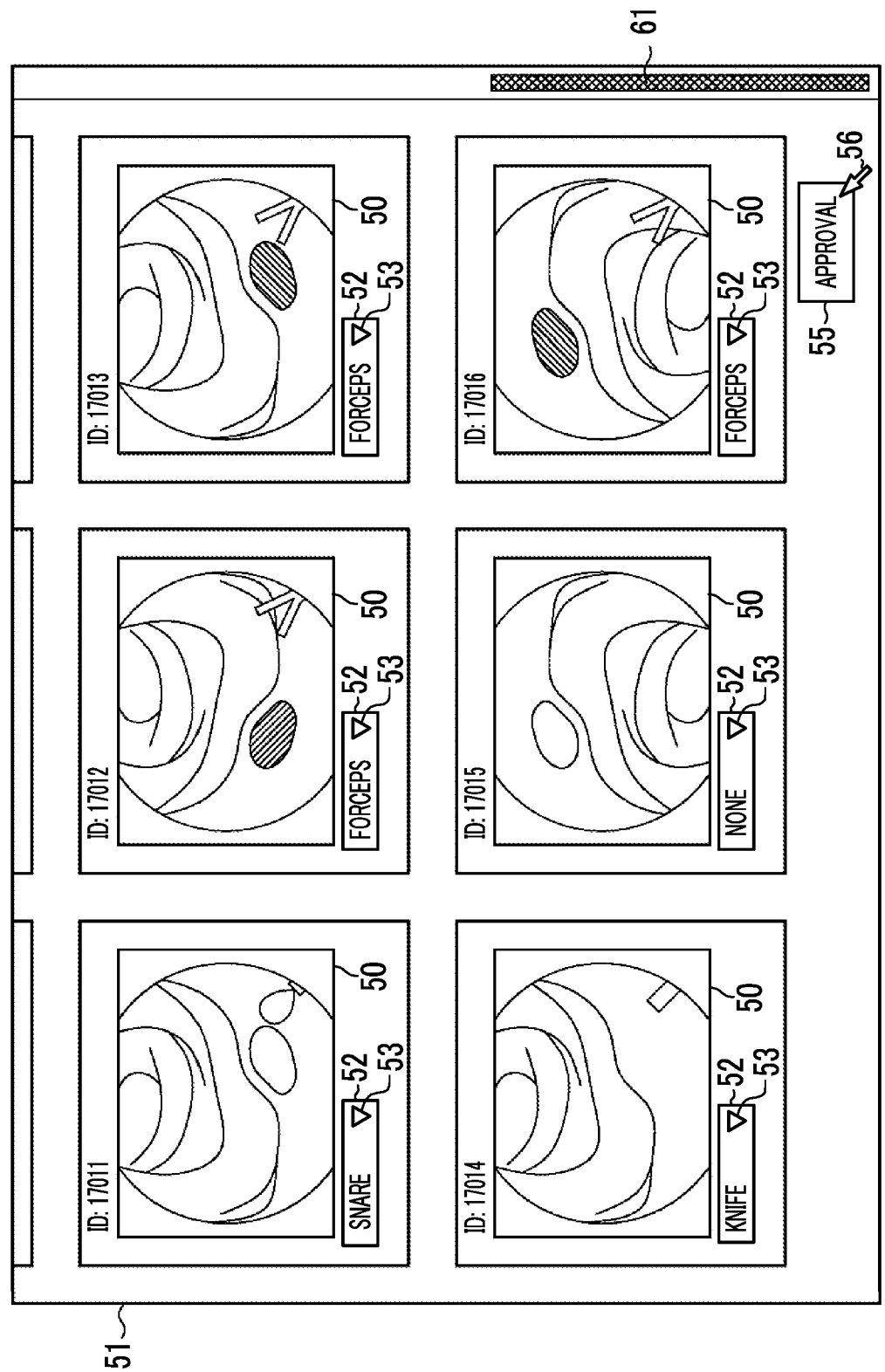
FIG. 13 is a display screen on which a plurality of medical images are displayed.

In FIGS. 9 and 10, a plurality of the medical images 50 to be displayed are all contained in the display screen 51, but depending on a size of the medical image 50 and the display screen 51, all of the medical images 50 may not be contained on the display screen 51. In this case, as shown in FIGS. 12 and 13, the operation display control section 48 displays a scroll bar 61 for scrolling display contents of the display screen 51. Accordingly, it is possible to display the medical images 50 that do not fit at a time on the display screen 51. In a case where it is possible to display a plurality of the medical images 50 using the scroll bar 61 and the approval operation is performed using the representative approval button 55 for giving the approval to the combination of all of the medical images 50 and the analysis results simultaneously, the representative approval button 55 is preferably displayed on the display screen 51 after scrolling (refer to FIG. 13) (in particular, a lower end of the display screen 51 after scrolling). Accordingly, in a case where the representative approval button 55 is provided on the display screen 51 after scrolling, it is possible to prevent the approval operation from being performed without checking the medical image 50 to be displayed on the display screen 51, that is the medical image 50 not yet displayed on the display screen 51.

Figure 14:
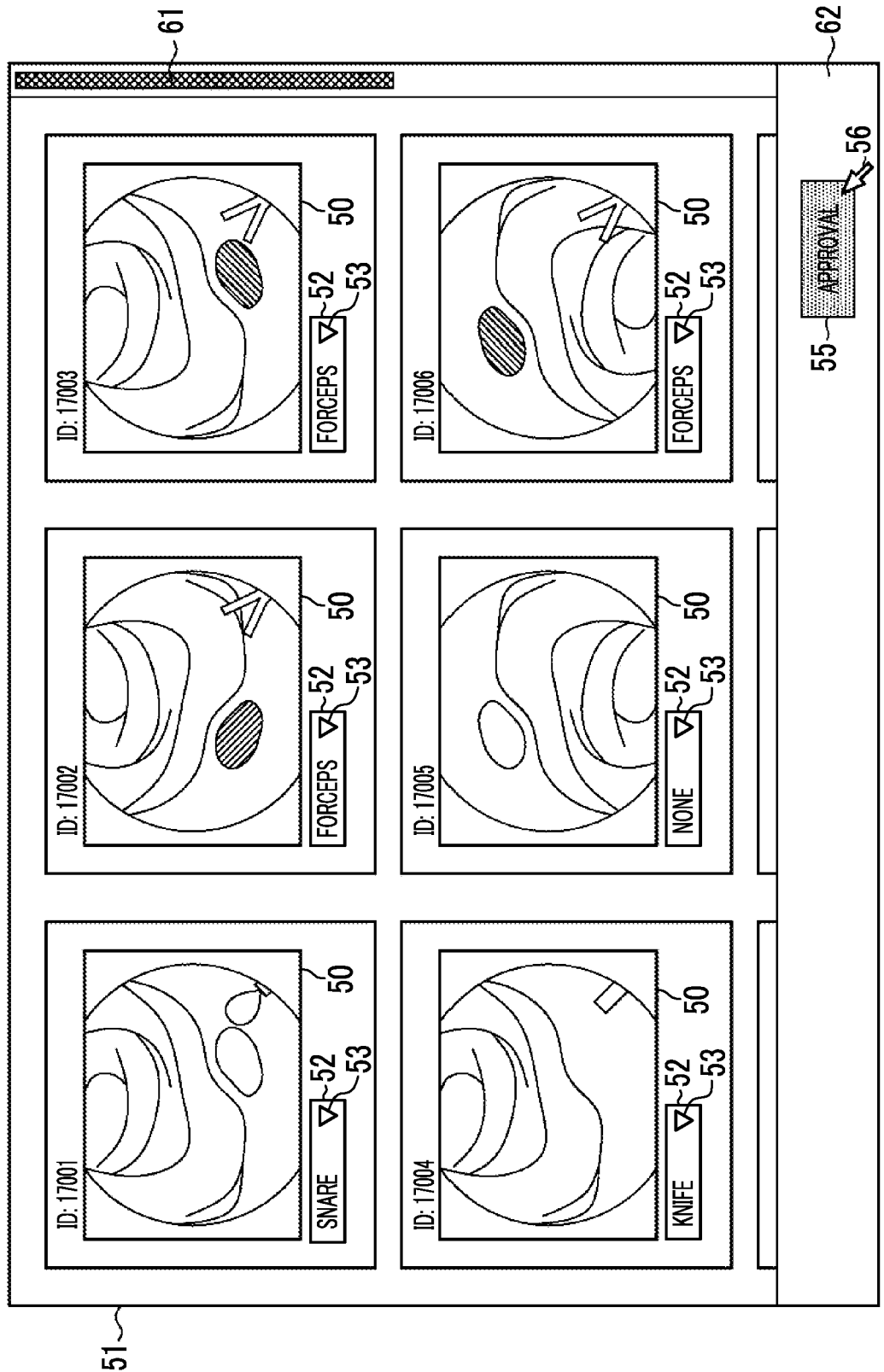
FIG. 14 is a display screen on which a plurality of medical images are displayed.
Figure 15:
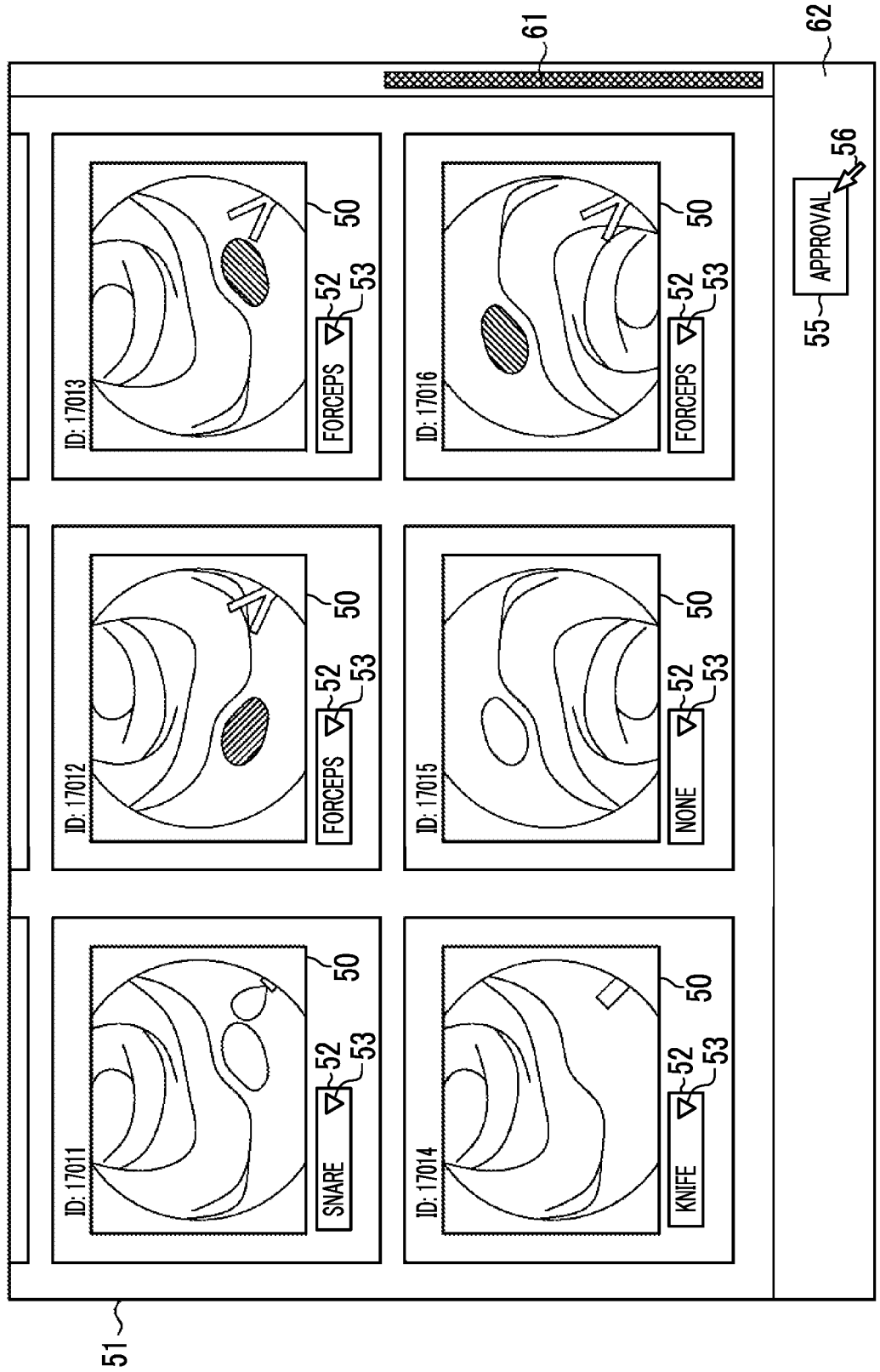
FIG. 15 is a display screen on which a plurality of medical images are displayed.

In addition, in a case where the representative approval button 55 is displayed at a display position other than a display position shown in FIGS. 12 and 13, it is preferable that the operation display control section 48 validates the representative approval button 55 after displaying all of the medical images 50 to be displayed at least once. For example, as shown in FIGS. 14 and 15, a constant display field 62 that is constantly displayed on the display screen 51 without depending on a position (operation state) of the scroll bar 61 is provided, and the representative approval button 55 is displayed in the constant display field 62. In this case, the operation display control section 48 invalidates the approval operation on the display screen 51 before scrolling (refer to FIG. 14). The invalidation of the approval operation means that the input receiving unit 14 does not receive the approval operation by clicking the approval button 55 and the like. The invalidation of the approval operation includes that the operation display control section 48 does not display the approval button 55 (display is hidden) even in a case where the input receiving unit 14 can receive the input of the click operation of the approval button 55, so as to be a state where the approval operation cannot be performed.

Then, the operation display control section 48 validates the approval operation in a case where the display screen 51 after scrolling (refer to FIG. 15) is displayed at least once and, as a result, it is confirmed that all of the medical images 50 to be displayed are displayed at least once. The validation of the approval operation means a state where the input receiving unit 14 can receive the approval operation by clicking the approval button 55 and the like, and, in addition to this, a state where the approval operation can be performed without lacking the display necessary for the approval operation.

As described above, in a case where the approval operation is invalidated or validated, it is possible to prevent the approval operation from being performed without checking the medical image 50 to be displayed on the display screen 51, that is the medical image 50 not yet displayed on the display screen 51. The same applies to a case where the representative approval button 55 is displayed in a pop-up manner or the like instead of providing the constant display field 62.

Further, in FIGS. 12 to 15 in which the scroll bar 61 is displayed, the representative approval button 55 for giving the approval to the combination of all of the medical images 50 and the analysis results simultaneously is provided. However, even in a case where the scroll bar 61 is displayed, the separate approval button 55 can be provided for each of a plurality of medical images 50.

Third Embodiment

In the second embodiment, the approval operation can be performed for all of a plurality of medical images 50 and the display of the analysis results displayed on the display screen 51. However, it is preferable to allow the combination of the medical images 50 and the analysis results for which the approval operation can be performed, to be selected optionally. In this case, the operation display control section 48 provides the display screen 51 with a selection unit 63 (refer to FIG. 16) for selecting one or more medical images 50 or one or more analysis results relating to the medical images 50. Then, the input receiving unit 14 receives an input regarding whether or not the analysis results relating to the medical images 50 selected by the selection unit 63 (in the present embodiment, "information on presence or absence of a treatment tool or a type of a treatment tool") or the analysis results selected by the selection unit 63 (in the present embodiment, at least "information on presence or absence of a treatment tool or a type of a treatment tool" among the selected analysis results) are correct. In addition, the input receiving unit 14 receives an input of the correction information for the analysis results relating to the medical images 50 selected by the selection unit 63 or the analysis results selected by the selection unit 63.

Figure 16:
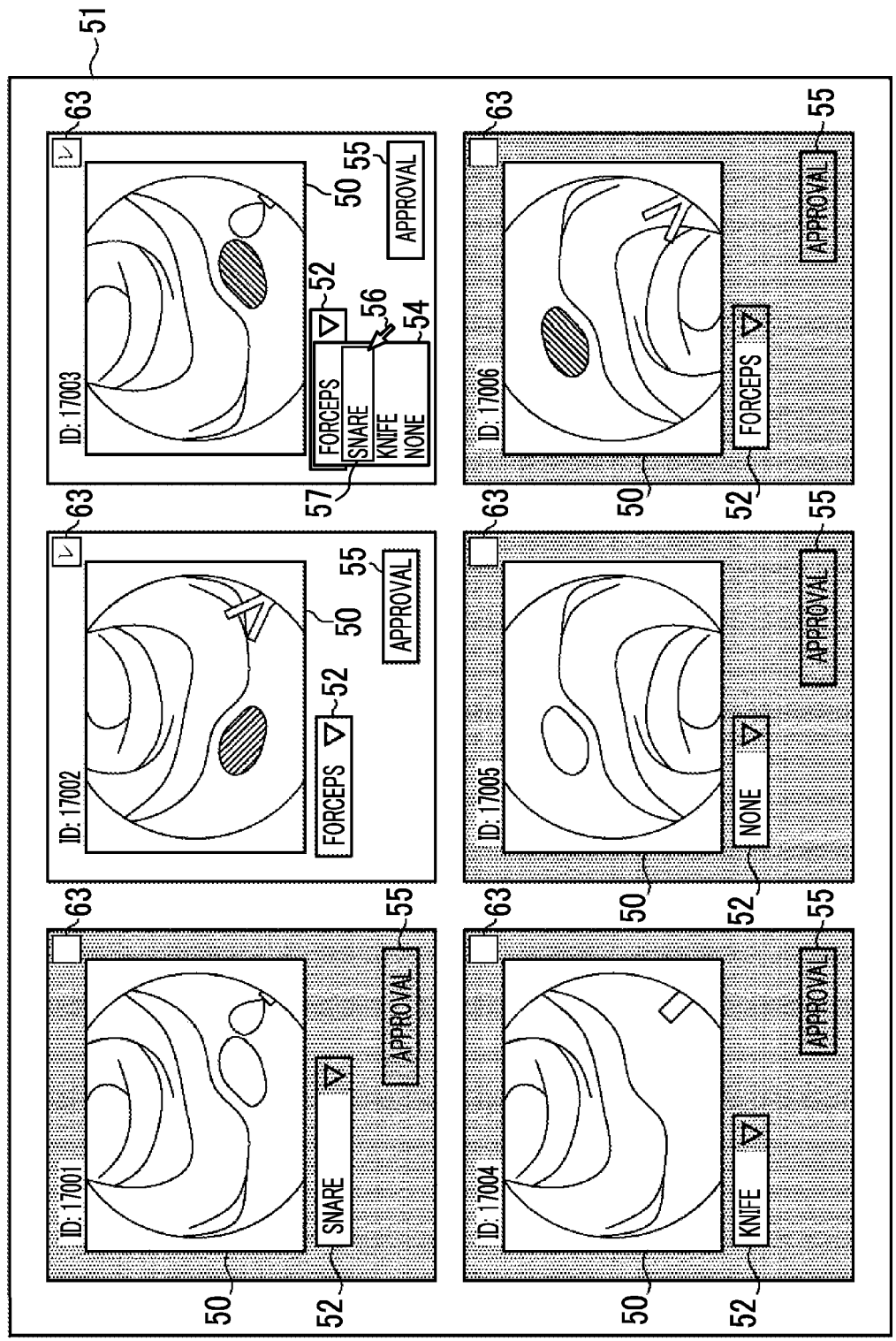
FIG. 16 is a display screen provided with a selection unit.

For example, as shown in FIG. 16, a check box is provided as the selection unit 63 for each medical image 50 displayed on the display screen 51. Then, the pull-down menu display button 53 and the approval button 55 are validated only for the medical image 50 and the analysis result that are checked in the check box which is the selection unit 63 with a mark ("v" mark in FIG. 16), and an input of the correction information and an approval operation are received only for the checked medical image and the analysis result. In this way, even in a case where a plurality of medical images 50 are displayed on the display screen 51, an input of an approval operation or correction information can be performed for each medical image 50.

In FIG. 16, the selection unit 63 is provided for each medical image 50, but the selection unit 63 can be provided for each analysis result. In this case, correction information can be input for each analysis result. In particular, in a case where there are a plurality of analysis results for one medical image 50 and a plurality of analysis results for one medical image 50 are displayed on the display screen 51, in a case where the selection unit 63 is provided for each of a plurality of displayed analysis results, it is possible to selectively input correction information for any analysis result among a plurality of analysis results to be displayed.

Further, the selection unit 63 can be provided for each medical image 50 and for each analysis information. In addition, in FIG. 16, an approval button 55 is provided for each medical image 50, but, as shown in the second embodiment, instead of providing an approval button 55 for each medical image 50, a representative approval button 55 can be provided. By doing so, it is possible to perform the approval operation for the medical images 50 selected by the selection unit 63 simultaneously.

Fourth Embodiment

Figure 17:
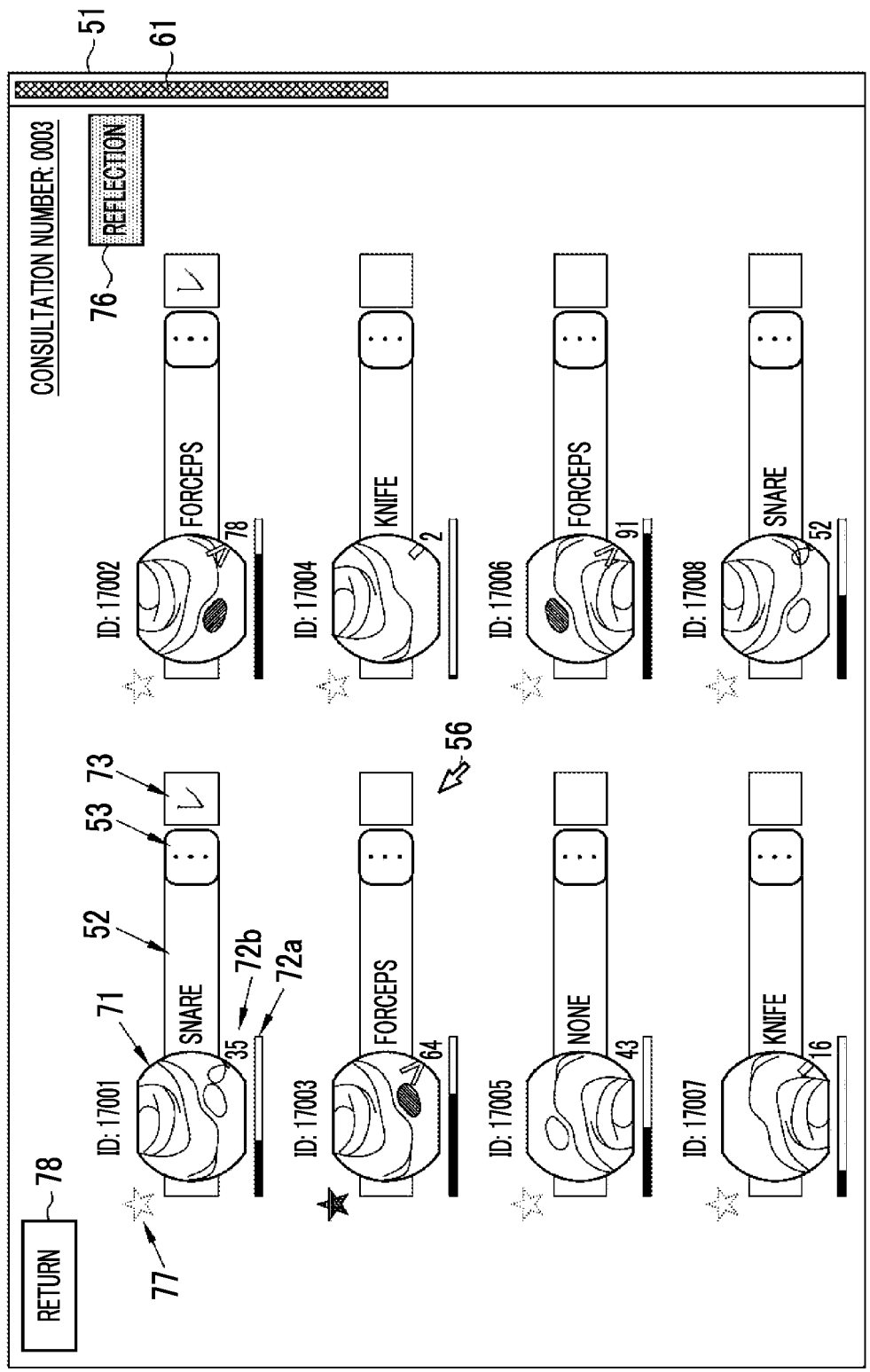
FIG. 17 is a display screen on which a minified image is displayed.
Figure 18:
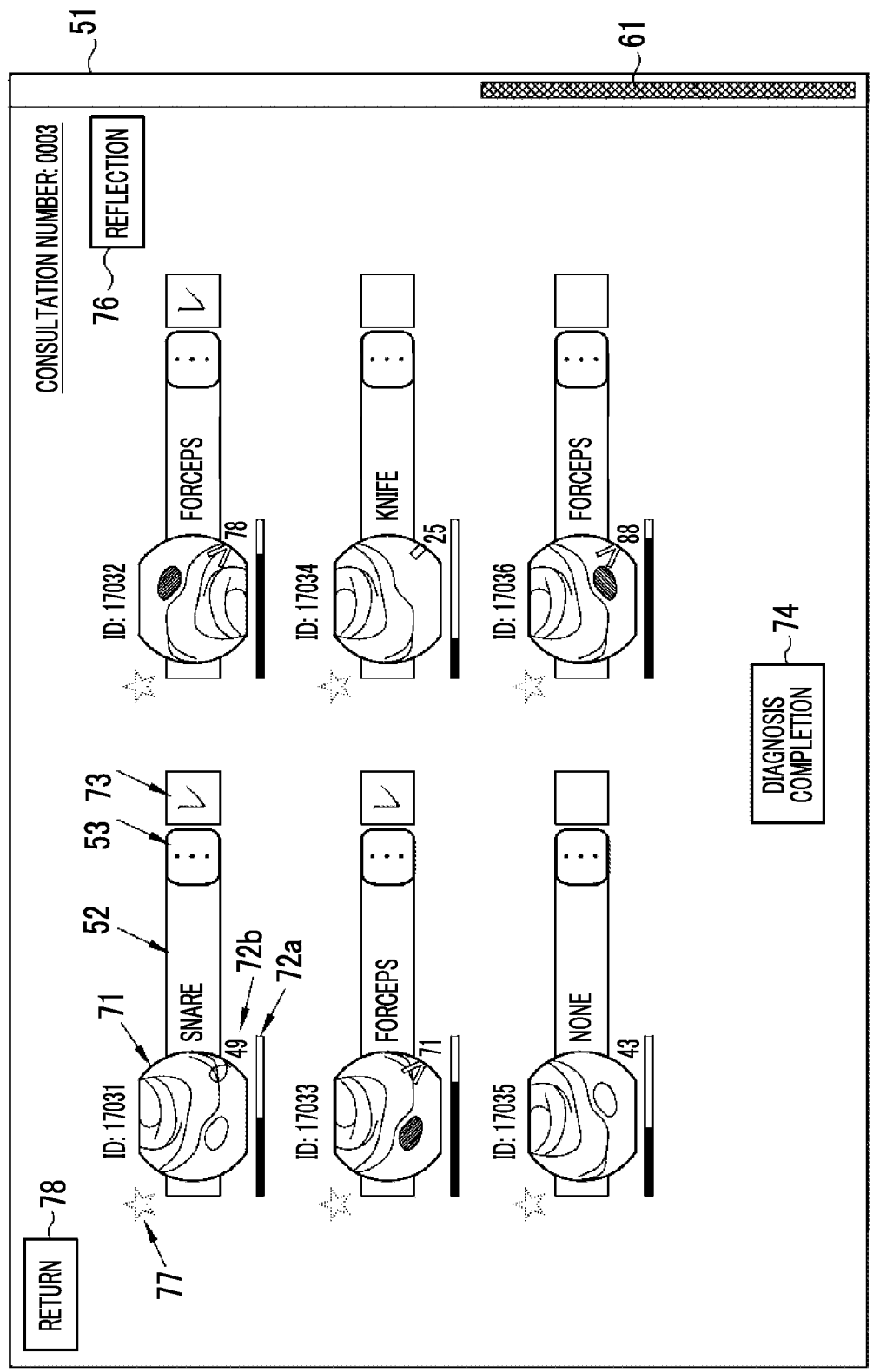
FIG. 18 is a display screen on which a minified image is displayed.
Figure 19:
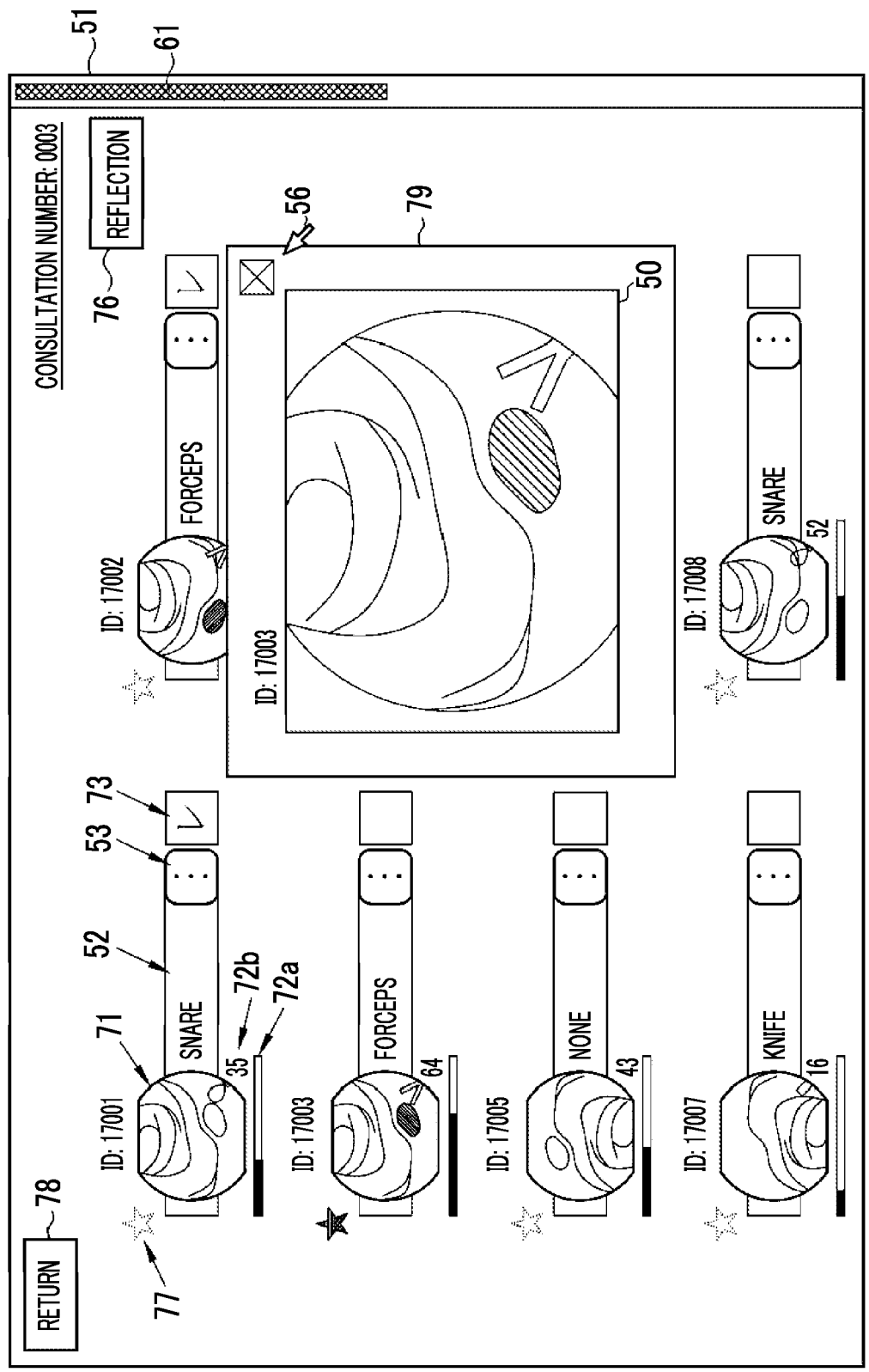
FIG. 19 is a display screen on which a minified image is displayed.

In the above first embodiment, second embodiment, and third embodiment, although the medical image 50 to be displayed on the display screen 51 is displayed on the display screen 51, but, in the display screen 51 in which an approval operation is performed, a minified image (so-called thumbnail image) 71 of the medical image 50 may be displayed. In this case, for example, as shown in FIGS. 17 to 19, a listing performance on the display screen 51 is improved. For this reason, in addition to the analysis result shown in the analysis result display field 52, a score 72a, a score 72b, and the like of an index used for obtaining the analysis result can be further displayed on the display screen 51. The score 72a and the score 72b are indices representing a probability of the analysis result output from the medical image analysis processing unit 37, a likelihood of a lesion, or the like, for example. In addition, in a case where the input receiving unit 14 receives an operation input by clicking on the minified image 71, the operation display control section 48 displays the medical image 50 that is an original image of the minified image 71 on which a click operation has been performed, on a pop-up window 79, for example (refer to FIG. 19). For this reason, even in a case where in the display screen 51 in which the approval operation is performed, the medical image 50 is displayed using the minified image 71, the doctor can make discrimination or diagnosis using the medical image 50 optionally and easily.

A check box 73 is a check box for showing that the medical image 50 and the analysis result have been checked. Then, in a case where all of the check boxes 73 are in a checked state ("V" mark in FIGS. 17 to 19), the input receiving unit 14 or the operation display control section 48 validates a diagnosis completion button 74 in the display screen 51 after scrolling (refer to FIG. 18). The diagnosis completion button 74 is a button for completing diagnosis and switching the display screen 51 to another screen, but is substantially used for an approval operation. That is, the diagnosis completion button 74 corresponds to the representative approval button 55 in the second embodiment or the third embodiment.

A reflection button 76 is a button used for the approval operation. Specifically, for at least one of the minified images 71 to be displayed on the display screen 51, in a case where the analysis result displayed in the analysis result display field 52 is corrected, in a case where the medical image 50 is displayed in the pop-up window 79, or in a case where a state of the check box 73 is changed, the operation display control section 48 validates the reflection button 76. The operation of the medical image processing apparatus 10 performed in a case where the reflection button 76 is clicked is the same as that in the first embodiment, the second embodiment, or the third embodiment.

In addition, a star 77 is an identification flag attached to the minified image 71 of the medical image 50 useful for creating a report. In a default state, for example, the star is white blank, and for the minified image 71 of the medical image 50 that is useful for creating a report, the star is shown in black. The determination regarding whether or not it is the minified image 71 of the medical image 50 useful for creating a report can be made automatically by the medical image processing apparatus 10 or manually by a doctor. In a case where the medical image processing apparatus 10 determines automatically, for example, a usefulness determination unit (not shown) is provided in the overall control unit 17. Then, the usefulness determination unit determines whether or not the medical image 50 is useful for creating a report using analysis results such as an index value (score 72b or the like), for example. In a case where the analysis results include a determination result regarding whether or not the medical image is useful for creating the report, the medical image processing apparatus 10 uses the determination result of the usefulness among the analysis results to determine a display form of the star 77. In a case of manually correcting the display form of the star 77 according to the determination of the doctor, for example, the star 77 is clicked with the pointer 56.

Figure 20:
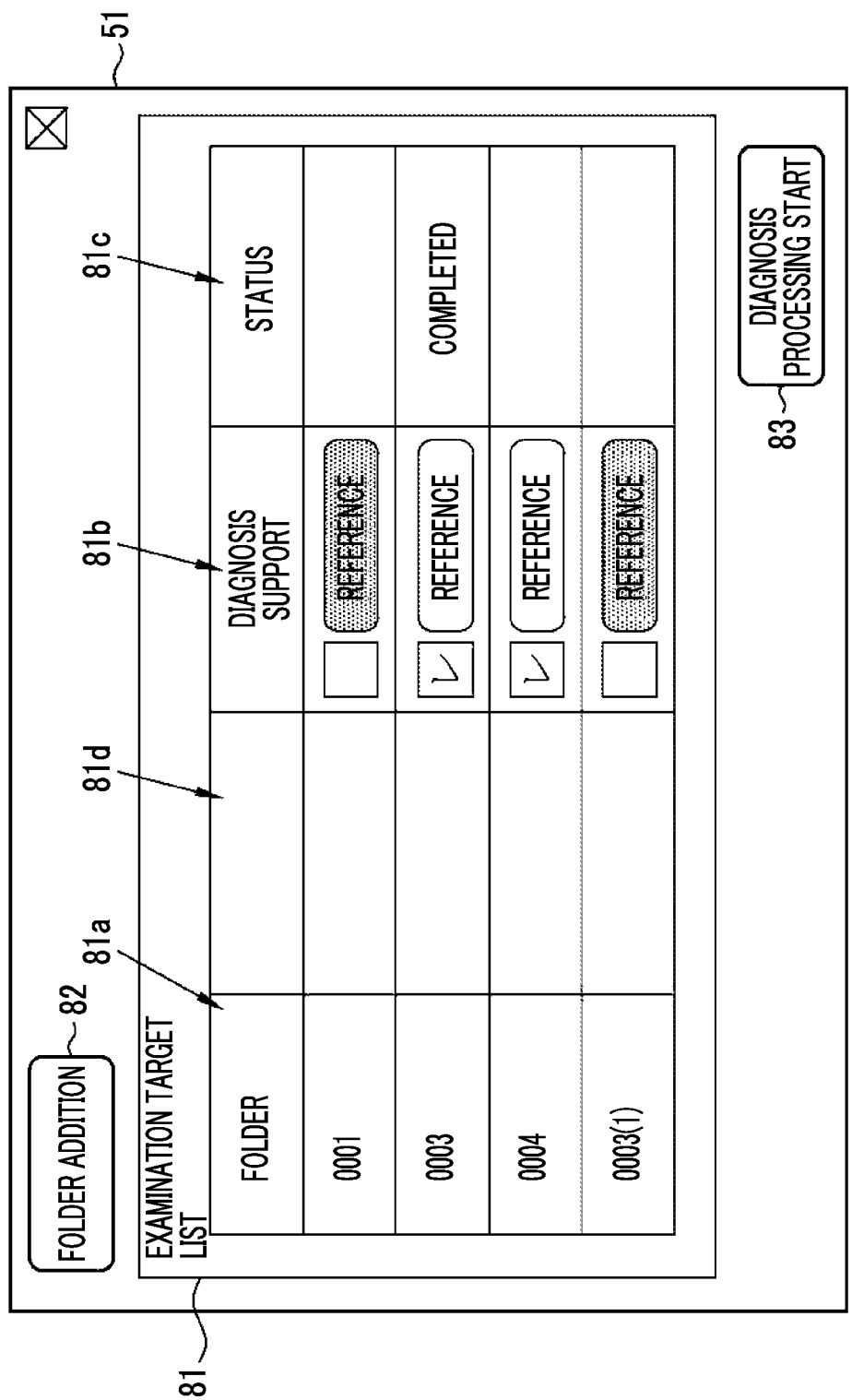
FIG. 20 is a menu screen.

A return button 78 is a button for returning to a previous screen such as a menu screen. A screen displayed in a case where the return button 78 is clicked has, for example, an examination target list 81, a folder addition button 82, a diagnosis processing start button 83, and the like on the display screen 51, as shown in FIG. 20. The examination target list 81 includes a folder field 81a, a diagnosis support field 81b, a status display field 81c, and another display field 81d. The status display field 81c is a field for displaying a status relating to diagnosis processing or the like for each folder, for example, "in correction", "in correction (with biopsy)", "completed", or the like. The examination target list 81 can be sorted by using "in correction", "in correction (with biopsy)", "completed", or a blank status of the status display field 81c. In a case where the diagnosis processing start button 83 is clicked, the display screen 51 is switched to the state of FIG. 17. In addition, any folder can be added to the examination target list 81 by clicking the folder addition button 82.

Figure 21:
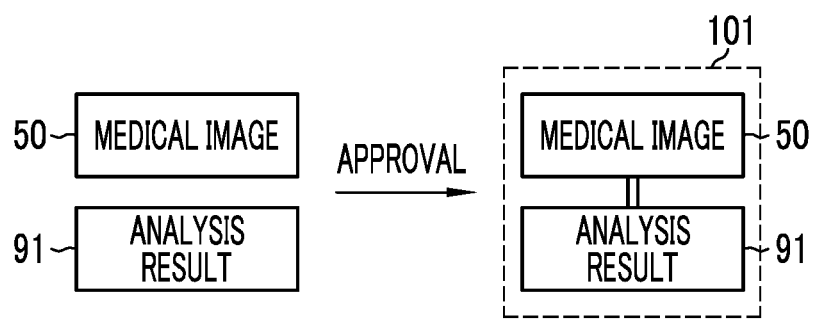
FIG. 21 is an explanatory diagram showing a storage aspect by a storage unit.
Figure 22:
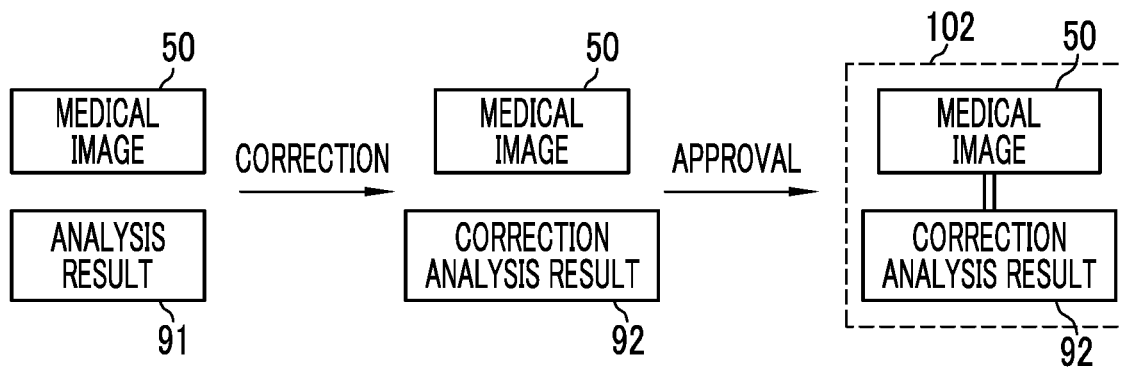
FIG. 22 is an explanatory diagram showing a storage aspect by a storage unit.

In the first embodiment, the second embodiment, the third embodiment, and the fourth embodiment, as shown in FIG. 21, in a case where there is an approval operation with respect to the combination of the medical image 50 and the analysis result 91, the storage unit 16 stores a set 101 of the medical image 50 and the analysis result 91, with the medical image 50 and the analysis result 91 being in association with each other. In addition, in a case where the analysis result 91 needs to be corrected, as shown in FIG. 22, the storage unit 16 stores a set 102 of a medical image 50 and a correction analysis result 92 obtained by correcting a part or all of the analysis results 91 relating to the medical image 50, with the medical image 50 and the correction analysis result 92 being in association with each other.

Figure 23:
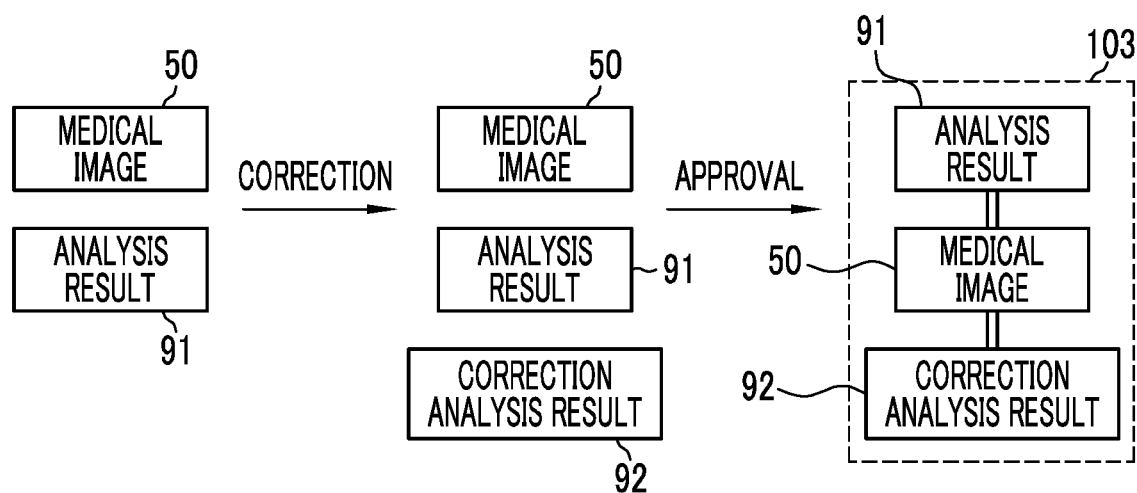
FIG. 23 is an explanatory diagram showing a storage aspect by a storage unit.

However, the storage form of the medical image 50 and the analysis result 91 or the correction analysis result 92 by the storage unit 16 is not limited to this. For example, as shown in FIG. 23, in a case where the analysis result 91 relating to the medical image 50 is corrected, the storage unit 16 can store a set 103 of the medical image 50, the analysis result 91 before correction, and the correction analysis result 92 obtained by replacing a part or all of the analysis results 91 with contents of correction information, with the medical image, the analysis result, and the correction analysis result being in association with one another. Furthermore, in the first embodiment, the second embodiment, the third embodiment, the fourth embodiment, or each example shown in FIGS. 21 and 22, the storage unit 16 may store a flag (data for identification) indicating that approval has been performed in association with one or a plurality of the medical image 50, the analysis result 91 before correction, or the correction analysis result 92. In addition, at this time, identification information such as a name or ID of the user who has performed the approval operation may be stored in association with each other.

Figure 24:
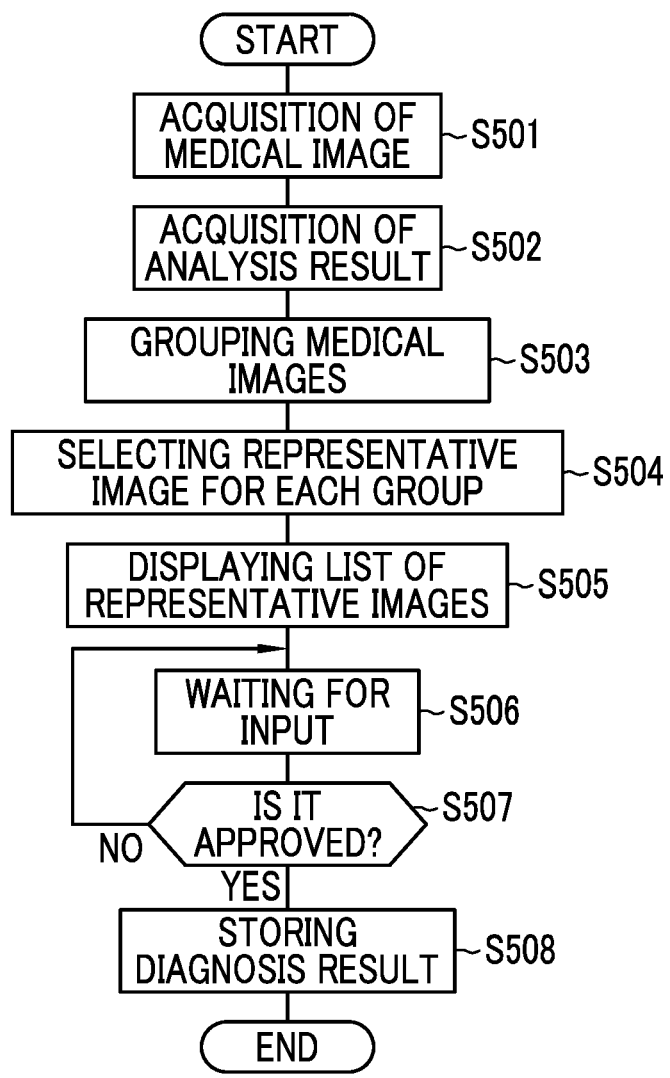
FIG. 24 is a flowchart in a case of grouping medical images.

In the first embodiment, the second embodiment, the third embodiment, and the fourth embodiment, the medical images 50 acquired by the medical image acquisition unit 11 are basically all displayed on the display screen 51, but the display unit 13 can select a part of a plurality of medical images 50 acquired by the medical image acquisition unit 11 to display the selected medical images on the display screen 51. In this case, for example, as shown in FIG. 24, the medical image acquisition unit 11 acquires a plurality of medical images 50 from the endoscope apparatus 21 or the like automatically or by manual selection (step S501). In addition, the medical image analysis result acquisition unit 12 acquires analysis results relating to a plurality of medical images 50 from the endoscope apparatus 21 or the like automatically or by manual selection (step S502).

Thereafter, the medical image display control section 46 groups a plurality of medical images 50 acquired by the medical image acquisition unit 11 (step S503). The medical image display control section 46 groups plurality of medical images 50 using, for example, each analysis result relating to a plurality of medical images 50, a score of a feature amount, similarity, or the like calculated uniquely by the medical image display control section 46, or other information such as an imaging time or an imaging part. As a result, a plurality of medical images 50 belong to any group of a group of "forceps", a group of "snare", a group of "knife", or a group of "none", for example. In addition, the medical image display control section 46 selects a representative image for each group (S504). The representative image of each group is selected according to a preset rule using, for example, a brightness of the medical image 50 or a type or a color of forceps in the case of a forceps group.

As described above, in a case where the medical image display control section 46 selects the representative image of each group, the display unit 13 displays the representative image (or the minified image of the representative image) of each group on the display screen 51. As described above, in a case where the medical image acquisition unit 11 acquires a plurality of medical images 50, a plurality of medical images 50 acquired by the medical image acquisition unit 11 are grouped and the representative image of each group is displayed on the display screen 51. In this case, it is possible to observe a small number of characteristic medical images 50 such as the representative image of each group and to approximately complete discrimination or diagnosis. Therefore, the doctor can easily make discrimination or diagnosis.

Further, a display aspect such as the representative image of each group and an operation aspect (steps S506 to S508) such as the approval operation after displaying the representative image of each group on the display screen 51 are the same as those in the first embodiment.

Figure 25:
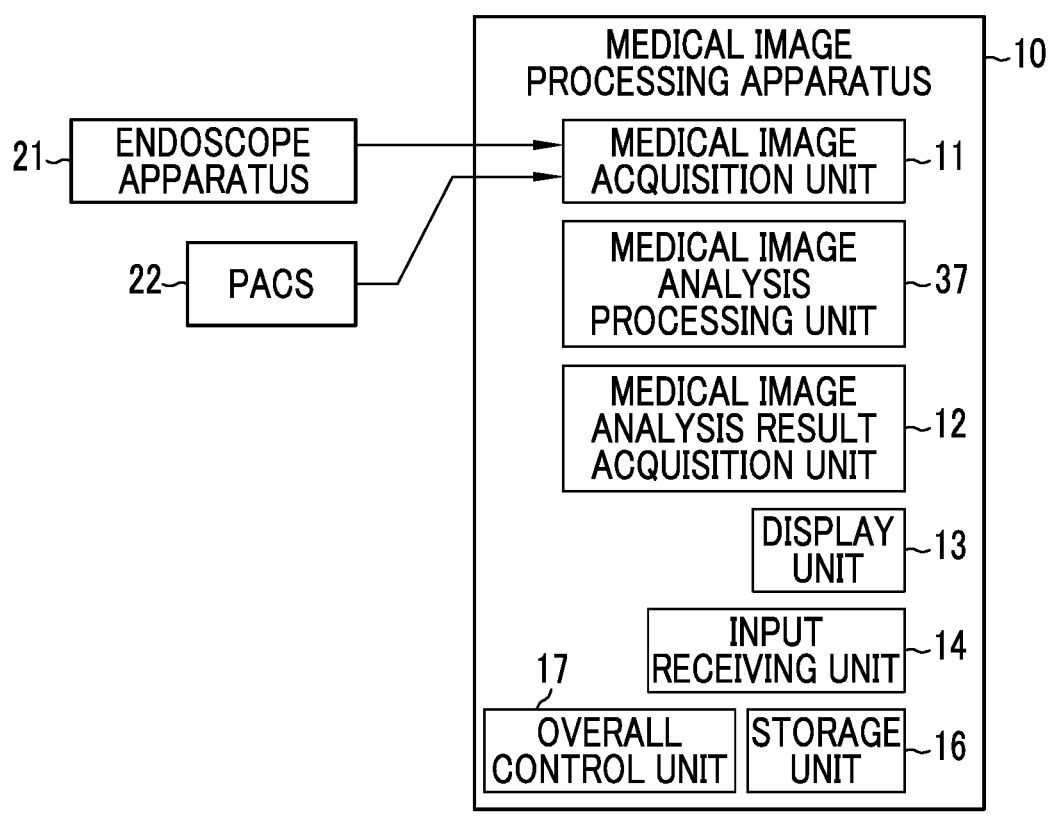
FIG. 25 is a block diagram of a medical image processing apparatus having a medical image analysis processing unit.

In the first embodiment, the second embodiment, the third embodiment, the fourth embodiment, and other modification examples, the medical image analysis processing unit 37 is provided in the processor device 33 of the endoscope apparatus 21. However, as shown in FIG. 25, the medical image analysis processing unit 37 can be provided in the medical image processing apparatus 10. In this case, the medical image analysis result acquisition unit 12 can acquire the analysis result from the medical image analysis processing unit 37 provided in the medical image processing apparatus 10.

Figure 26:
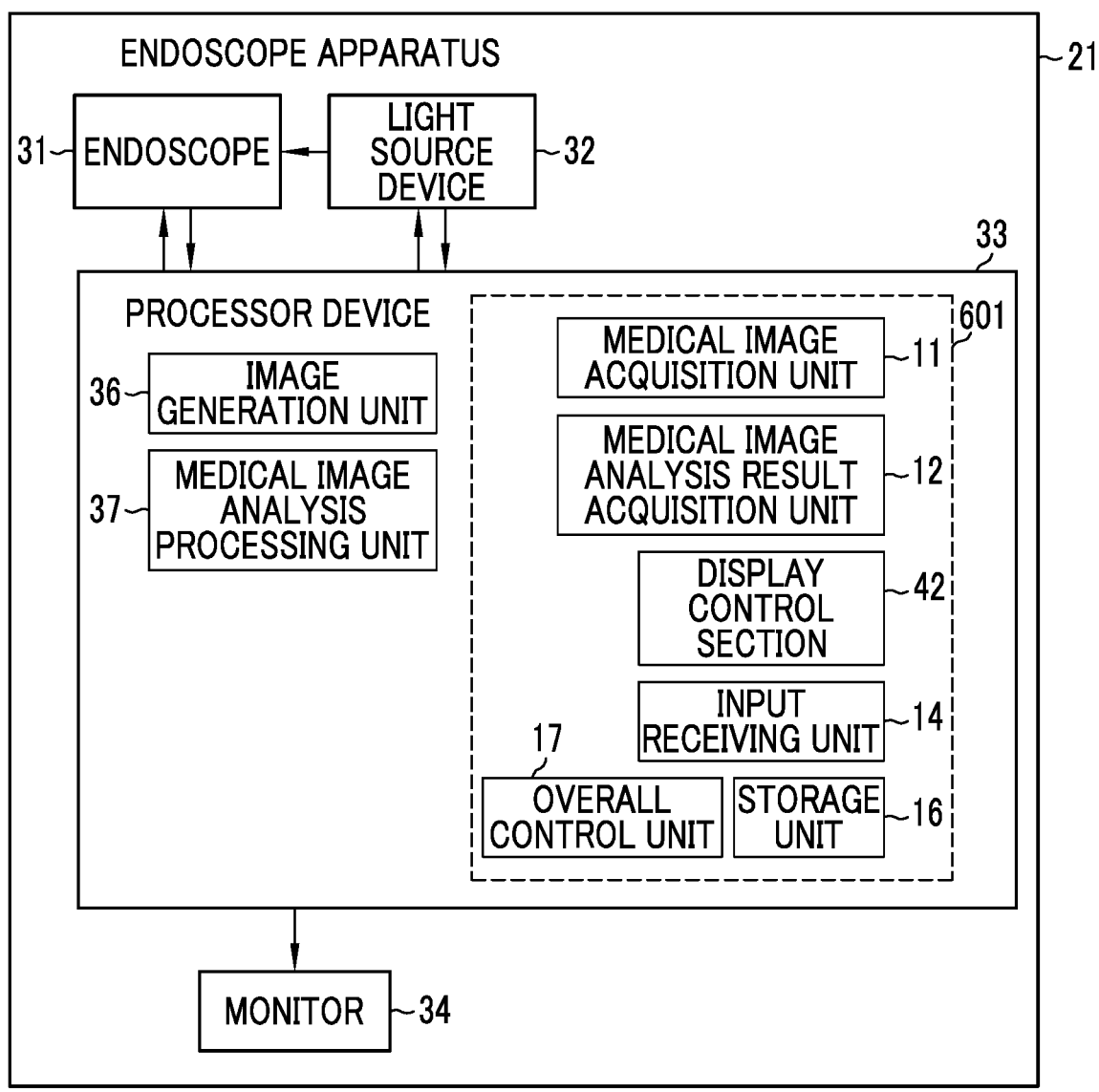
FIG. 26 is an endoscope apparatus including a medical image processing apparatus.

In addition, the endoscope apparatus 21 can include the medical image processing apparatus 10. In this case, as shown in FIG. 26, each unit 601 forming the medical image processing apparatus 10 is provided in the processor device 33. Here, since the display 41 of the display unit 13 can be commonly used as the monitor 34 of the endoscope apparatus 21, it is sufficient to provide the processor device 33 with the display control section 42 that is a part of the display unit 13, instead of the display unit 13. In addition, a new endoscope apparatus can be configured by all of the medical image processing apparatus 10 of each of the first embodiment, the second embodiment, the third embodiment, the fourth embodiment, and other modification examples, and the endoscope apparatus 21 shown in FIG. 2.

Figure 27:
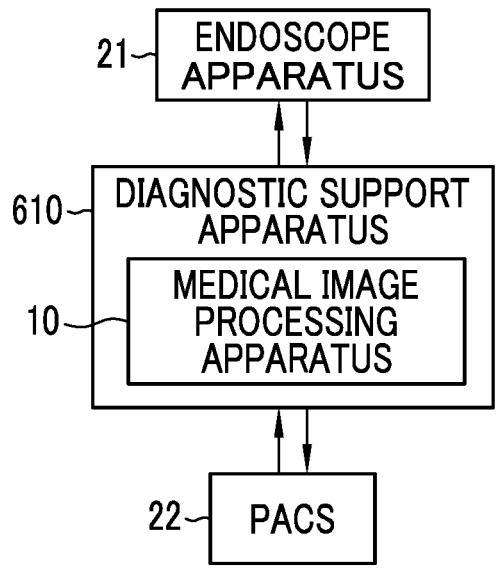
FIG. 27 is a diagnostic support apparatus including a medical image processing apparatus.
Figure 28:
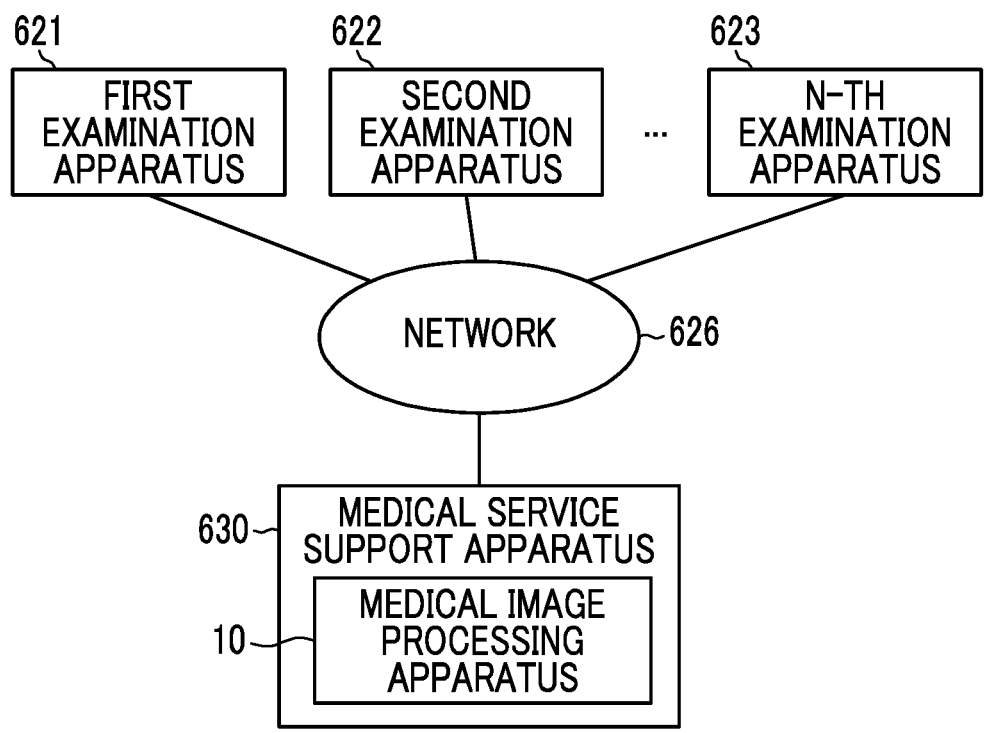
FIG. 28 is a medical service support apparatus including a medical image processing apparatus.

In addition, as shown in FIG. 27, a diagnostic support apparatus 610 used in combination with other modalities such as the endoscope apparatus 21 can include the medical image processing apparatus 10 of each of the first embodiment, the second embodiment, the third embodiment, the fourth embodiment, and other modification examples. In addition, as shown in FIG. 28, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatus 10 of each of the first embodiment, the second embodiment, the third embodiment, the fourth embodiment, and other modification examples.

Figure 29:
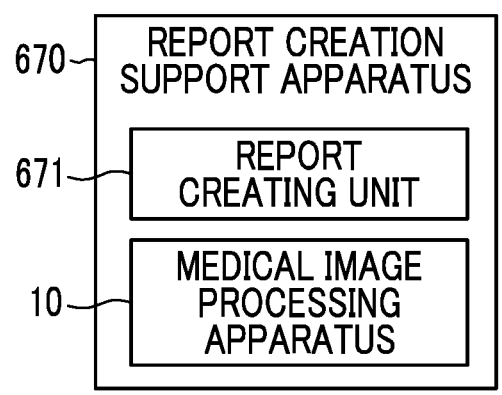
FIG. 29 is a report creation support apparatus including a medical image processing apparatus.
Figure 30:
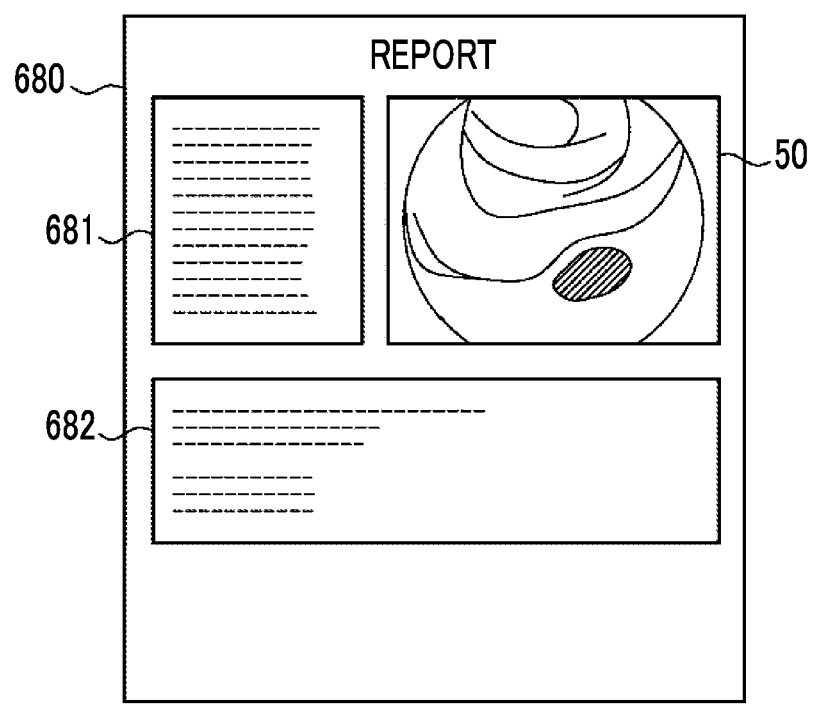
FIG. 30 is an example of a report.

In addition, as shown in FIG. 29, a report creation support apparatus 670 that supports a doctor in creating a report, is configured to comprise a report creating unit 671 that creates a report using the analysis result, and the medical image processing apparatus 10 of each of the first embodiment, the second embodiment, the third embodiment, the fourth embodiment, and other modifications. As shown in FIG. 30, a report 680 that is created by the report creating unit 671 has, for example, a display field for the medical image 50, a basic input field 681 for inputting information such as a patient or an examination, and an opinion input field 682 for inputting an opinion of a doctor. The report creating unit 671 or the medical image processing apparatus 10 can automatically insert the medical image 50 approved by the doctor in the medical image processing apparatus 10 into the report 680. In addition, the report creating unit 671 or the medical image processing apparatus 10 can automatically insert the analysis result (including the correction analysis result 92 or the combination of the analysis result 91 and the correction analysis result 92) approved by the doctor in the medical image processing apparatus 10 into the basic input field 681, the opinion input field 682, or both of these fields. As described above, in a case where the medical image 50, the information of the analysis result, or the like approved by the doctor in the medical image processing apparatus 10 is automatically inserted, it is possible to easily create a report.

In addition to this, the medical image processing apparatus 10, various apparatuses including the medical image processing apparatus 10, and various apparatuses or systems having a function of the medical image processing apparatus 10 can be used by making the following various changes or the like.

The medical image analysis processing unit 37 can detect a region of interest that is a region to be observed, based on the feature amount of a pixel of the medical image 50, and obtain at least information on presence or absence of a treatment tool or a type of a treatment tool for the region of interest. In a case where the endoscope apparatus 21 or the like comprises the medical image analysis processing unit 37, the medical image analysis result acquisition unit 12 can acquire the analysis result from the medical image analysis processing unit 37.

The medical image analysis result acquisition unit 12 can acquire the analysis result from a recording apparatus that records the analysis result relating to the medical image 50. A storage (not shown) provided in a management system such as the PACS 22, other information systems, the endoscope apparatus 21, or the like, or other external storages such as a network attached storage (NAS) are examples of the recording apparatus.

As the medical image 50, it is possible to use a normal light image obtained by emitting light in a white band or light in a plurality of wavelength bands as the light in the white band.

In a case where an image obtained by emitting light in a specific wavelength band is used as the medical image 50, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that the light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that the light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and the light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and the light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that the light in the specific wavelength band has a peak wavelength within the wavelength band of 400±10 nm, 440±10 nm, 470±10 nm, or 600 nm to 750 nm.

In a case where the medical image 50 is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image 50 is an in-vivo image of the living body, the wavelength band of infrared light can be used as the specific wavelength band described above.

In a case where the medical image 50 is an in-vivo image of the living body and the wavelength band of infrared light is used as the specific wavelength band described above, it is preferable that the specific wavelength band includes a wavelength band of 790 nm to 820 nm or 905 nm to 970 nm and that the light in the specific wavelength band has a peak wavelength within the wavelength band of 790 nm to 820 nm or 905 nm to 970 nm.

The medical image acquisition unit 11 can have a special light image acquisition section that acquires a special light image having a signal in a specific wavelength band on the basis of a normal light image obtained by emitting light in a white band or light in a plurality of wavelength bands as the light in the white band. In this case, the special light image can be used as the medical image 50.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as the light in the white band or the special light image obtained by emitting light in a specific wavelength band. In this case, the feature amount image can be used as the medical image 50.

In the endoscope apparatus 21, a capsule endoscope can be used as the endoscope 31. In this case, the light source device 32 and a part of the processor device 33 can be mounted in the capsule endoscope.

In the embodiment described above, the hardware structures of processing units for executing various kinds of processing, such as the medical image acquisition unit 11, the medical image analysis result acquisition unit 12, the input receiving unit 14, the storage unit 16, the overall control unit 17, the image generation unit 36, the medical image analysis processing unit 37, the display control section 42, the medical image display control section 46, the analysis result display control section 47, the operation display control section 48, and the report creating unit 671 are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a dedicated circuit configuration for executing various types of processing, and the like.

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: medical image analysis result acquisition unit
13: display unit
14: input receiving unit
16: storage unit
17: overall control unit
21: endoscope apparatus
22: PACS
31: endoscope
32: light source device
33: processor device
34: monitor
36: image generation unit
37: medical image analysis processing unit
41: display
42: display control section
46: medical image display control section
47: analysis result display control section
48: operation display control section
50: medical image
51: display screen
52: analysis result display field
53: pull-down menu display button
54: pull-down menu
55: approval button
56: pointer
57: selection mark
61: scroll bar
62: constant display field
63: selection unit
71: minified image
72a, 72b: score
73: check box
74: diagnosis completion button
76: reflection button
77: star
78: return button
79: pop-up window 81: examination target list
81a: folder field
81b: diagnosis support field
81c: status display field
81d: another display field
82: folder addition button
83: diagnosis processing start button
91: analysis result
101: set of medical image and analysis result
102: set of medical image and correction analysis result
103: set of medical image, analysis result, and correction analysis result
601: each unit forming medical image processing apparatus
610: diagnostic support apparatus
621: first examination apparatus
622: second examination apparatus
623: N-th examination apparatus
626: network
630: medical service support apparatus
670: report creation support apparatus
671: report creating unit
680: report
681: basic input field
682: opinion input field

What is claimed is:

1. A medical image processing apparatus comprising:
a display; and
a processor configured to:
  acquire a medical image including a subject image;
  acquire an analysis result obtained by analyzing the medical image;
  display at least one medical image and at least information on presence or absence of a treatment tool or a type of a treatment tool in the analysis result to be approved on the display;
  detect a reception of an input for an approval to the information on presence or absence of a treatment tool or a type of treatment tool included in the analysis result;
  in response to the information on presence or absence of a treatment tool or a type of a treatment tool included in the analysis result being correct, receive the reception of the input for the approval to the analysis result; and
  in response to the information on presence or absence of a treatment tool or a type of a treatment tool included in the analysis result being incorrect, receive an input of correction information for correcting the information on presence or absence of a treatment tool or a type of a treatment tool included in the analysis result based on a corrected treatment tool selected from a pull-down menu comprising a plurality of candidates of treatment tools, and receive the reception of the input for the approval of the analysis result corresponding to the corrected information.

2. The medical image processing apparatus according to claim 1,
wherein the processor is further configured to select one or more medical images or one or more analysis results relating to the medical images, and
wherein the correction information is an information for correcting the information on presence or absence of a treatment tool or a type of a treatment tool relating to selected medical images or the information on presence or absence of a treatment tool or a type of a treatment tool relating to the analysis results of the selected medical images.

3. The medical image processing apparatus according to claim 1, further comprising:
a storage that stores both the analysis result and the correction information in association with the medical image relating to the analysis result and the correction information in a case where the processor receives the input of the correction information.

4. The medical image processing apparatus according to claim 2, further comprising:
a storage that stores both the analysis result and the correction information in association with the medical image relating to the analysis result and the correction information in a case where the processor receives the input of the correction information.

5. The medical image processing apparatus according to claim 1, further comprising:
a storage that stores the analysis result, a part or all of which are replaced with contents of the correction information, and the medical image relating to the analysis result, a part or all of which are replaced with contents of the correction information, in association with each other, in a case where the processor receives the input of the correction information.

6. The medical image processing apparatus according to claim 2, further comprising:
a storage that stores the analysis result, a part or all of which are replaced with contents of the correction information, and the medical image relating to the analysis result, a part or all of which are replaced with contents of the correction information, in association with each other, in a case where the processor receives the input of the correction information.

7. The medical image processing apparatus according to claim 1,
wherein the processor sequentially displays one or more medical images, or displays a plurality of the medical images collectively on the display, and
wherein the processor validates a reception of the input of the correction information after the processor displays all of the medical images to be displayed at least once on the display.

8. The medical image processing apparatus according to claim 2,
wherein the processor sequentially displays one or more medical images, or displays a plurality of the medical images collectively on the display, and
wherein the processor validates a reception of the input of the correction information after the processor displays all of the medical images to be displayed at least once on the display.

9. The medical image processing apparatus according to claim 3,
wherein the processor sequentially displays one or more medical images, or displays a plurality of the medical images collectively on the display, and
wherein the processor validates a reception of the input of the correction information after the processor displays all of the medical images to be displayed at least once on the display.

10. The medical image processing apparatus according to claim 4,
wherein the processor sequentially displays one or more medical images, or displays a plurality of the medical images collectively on the display, and wherein the processor validates a reception of the input of the correction information after the processor displays all of the medical images to be displayed at least once on the display.

11. The medical image processing apparatus according to claim 1,
wherein the processor is further configured to:
analyze the medical image by detecting a region of interest, which is a region to be observed, based on a feature amount of pixels of the medical image; and
obtain at least the information on presence or absence of a treatment tool or a type of a treatment tool for the region of interest as the analysis result.

12. The medical image processing apparatus according to claim 1,
wherein the processor acquires the analysis result from a recording apparatus that records the analysis result relating to the medical image.

13. The medical image processing apparatus according to claim 1,
wherein the processor displays at least one of an index representing a probability of the analysis result of the medical image or an index representing a likelihood of a lesion in the medical image together with a minified image of the medical image on the display.

14. The medical image processing apparatus according to claim 13,
wherein in a case where the processor receives an operation to designate the minified image, the processor displays the medical image that is an original image of the designated minified image with a pop-up window on the display.

15. The medical image processing apparatus according to claim 13,
wherein the processor displays a check box which shows that the medical images and the analysis results have been checked for each minified image on the display.

16. The medical image processing apparatus according to claim 1,
wherein the processor is further configured to:
group medical images for each type of a treatment tool based on the information on a type of a treatment tool in the analysis result;
select representative medical images for each group of the medical images grouped by treatment tool type; and
display a list of the representative medical images on the display.

17. The medical image processing apparatus according to claim 16,
wherein the processor is configured to select one or more the representative medical images, and
wherein the processor receives an input of an information for correcting the information on presence or absence of a treatment tool or a type of a treatment tool relating to the medical images of the group corresponding to the selected representative medical image as the correction information.

18. A diagnostic support apparatus comprising the medical image processing apparatus according to claim 1.

19. A medical service support apparatus comprising the medical image processing apparatus according to claim 1.

20. A report creation support apparatus comprising:
the medical image processing apparatus according to claim 1; and
a processor configured to create a report using the analysis result.

21. The medical image processing apparatus according to claim 1, wherein after displaying the medical image and the information on presence or absence of a treatment tool or a type of a treatment tool in the analysis result on the display, the processor is further configured to:
in response to the reception of the input for the approval of the analysis result being detected, store the medical image and the analysis result in association with each other; and
in response to the reception of the input for the approval of the analysis result not being detected, continue detecting the reception of the input for the approval of the analysis result.

22. A medical image processing apparatus comprising:
a display; and
a processor configured to:
acquire a medical image including a subject image;
acquire an analysis result obtained by analyzing the medical image, wherein the analysis result comprises information on an automatic detection of a type of treatment tool in the medical image;
display at least one medical image and the information on the type of the treatment tool in the analysis result to be approved on the display;
detect a reception of an input for an approval to the information on presence or absence of a treatment tool or a type of treatment tool included in the analysis result;
in response to the information on presence or absence of a treatment tool or a type of a treatment tool included in the analysis result being correct, receive the reception of the input for the approval to the analysis result; and
in response to the information on presence or absence of a treatment tool or a type of a treatment tool included in the analysis result being incorrect, receive an input of correction information for correcting the information on presence or absence of a treatment tool or a type of a treatment tool included in the analysis result based on a corrected treatment tool selected from a pull-down menu comprising a plurality of candidates of treatment tools, and receive the reception of the input for the approval of the analysis result corresponding to the correction information.

* * * * *